(12) United States Patent
Van den Heuvel

(10) Patent No.: US 8,798,757 B2
(45) Date of Patent: Aug. 5, 2014

(54) METHOD AND DEVICE FOR AUTOMATED OBSERVATION FITTING

(75) Inventor: Koen Van den Heuvel, Hove (BE)

(73) Assignee: Cochlear Limited, Macquarie University, NSW (AU)

(*) Notice: Subject to any disclaimer, the term of this patent is extended or adjusted under 35 U.S.C. 154(b) by 957 days.

(21) Appl. No.: 12/299,773

(22) PCT Filed: May 8, 2007

(86) PCT No.: PCT/US2007/068465
§ 371 (c)(1),
(2), (4) Date: Feb. 5, 2009

(87) PCT Pub. No.: WO2007/134048
PCT Pub. Date: Nov. 22, 2007

(65) Prior Publication Data
US 2009/0306743 A1 Dec. 10, 2009

Related U.S. Application Data

(60) Provisional application No. 60/798,312, filed on May 8, 2006.

(51) Int. Cl.
*A61N 1/36* (2006.01)
(52) U.S. Cl.
USPC .................. 607/57; 607/55; 607/56

(58) Field of Classification Search
CPC .......... A61B 5/12; A61B 5/121; A61B 5/123; A61B 5/125; A61N 1/36032
USPC ...................................... 607/55–57
See application file for complete search history.

(56) References Cited

U.S. PATENT DOCUMENTS

| | | | | |
|---|---|---|---|---|
| 3,938,500 | A * | 2/1976 | Simmons | 600/559 |
| 5,684,460 | A * | 11/1997 | Scanlon | 340/573.1 |
| 5,922,016 | A * | 7/1999 | Wagner | 607/137 |
| 6,205,360 | B1 | 3/2001 | Carter et al. | |
| 2001/0029313 | A1* | 10/2001 | Kennedy | 600/25 |
| 2006/0061545 | A1 | 3/2006 | Hughes et al. | |

OTHER PUBLICATIONS

International Search Report. PCT/US2007/068465. Mailed Mar. 17, 2008.

* cited by examiner

*Primary Examiner* — Allen Porter, Jr.
(74) *Attorney, Agent, or Firm* — K&L Gates, LLP

(57) ABSTRACT

Fitting an auditory prosthesis to a recipient by automatically determining operational thresholds of the prosthesis based on changes in the activity of the recipient that occur in response to applied stimulation signals. Such changes in recipient activity are detected by an inertial measurement unit (IMU) permanently or temporarily secured to or implanted in the recipient as an integral part of the prosthesis or a separate device operationally coupled to the prosthesis.

45 Claims, 19 Drawing Sheets

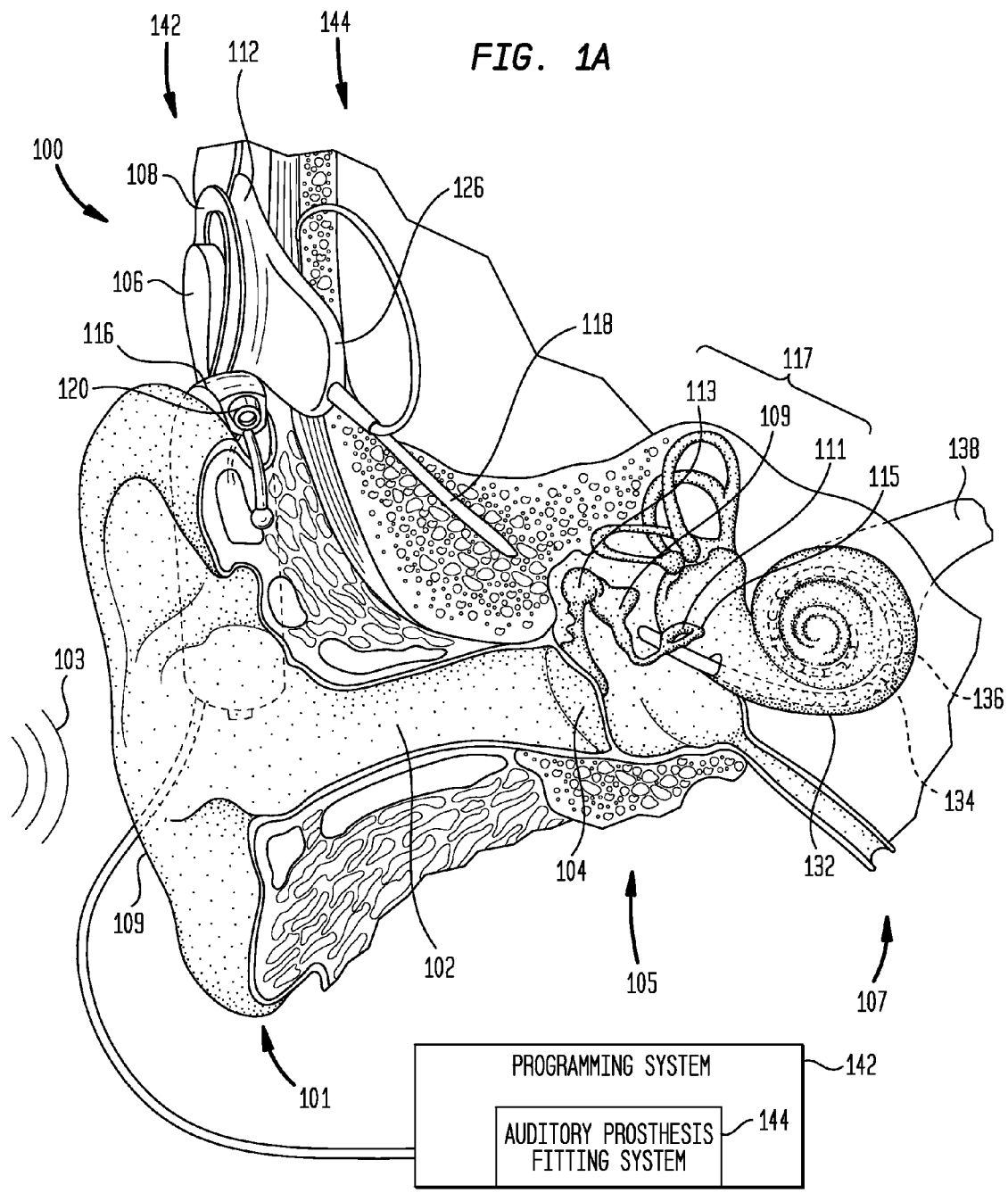

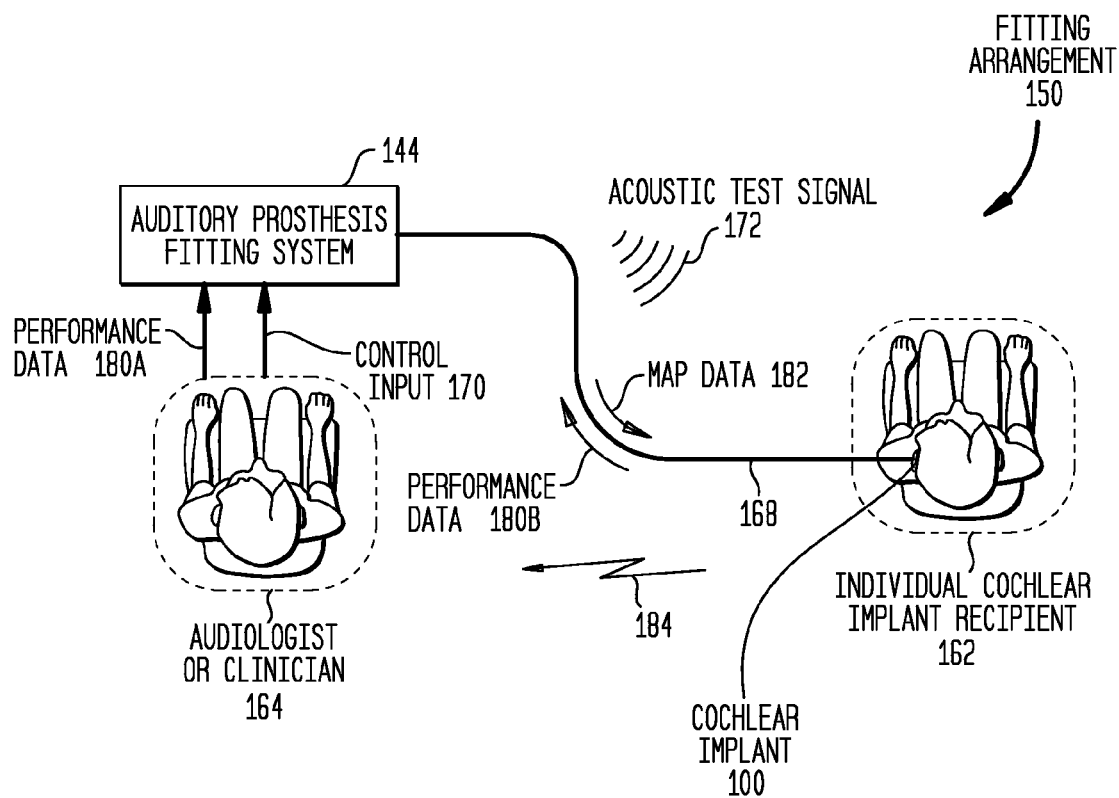

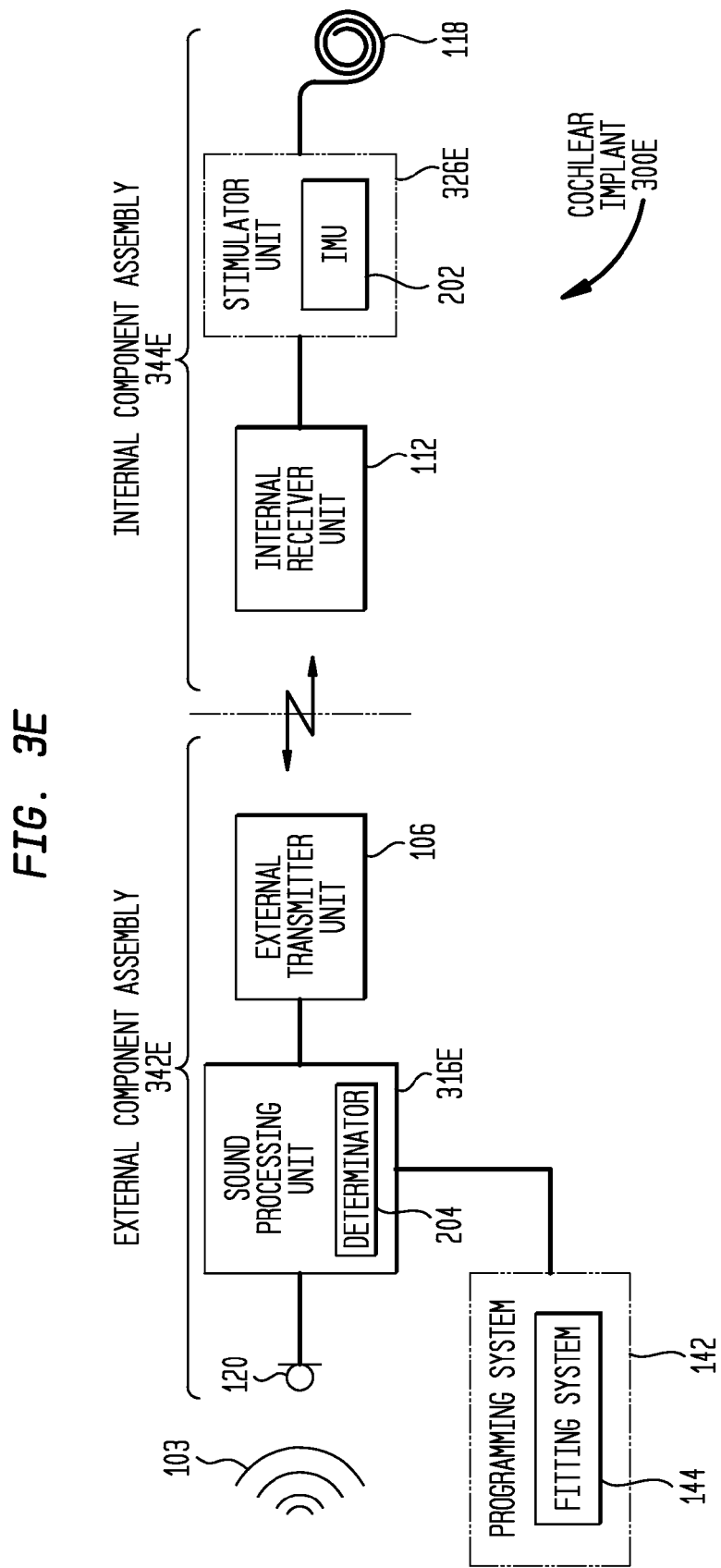

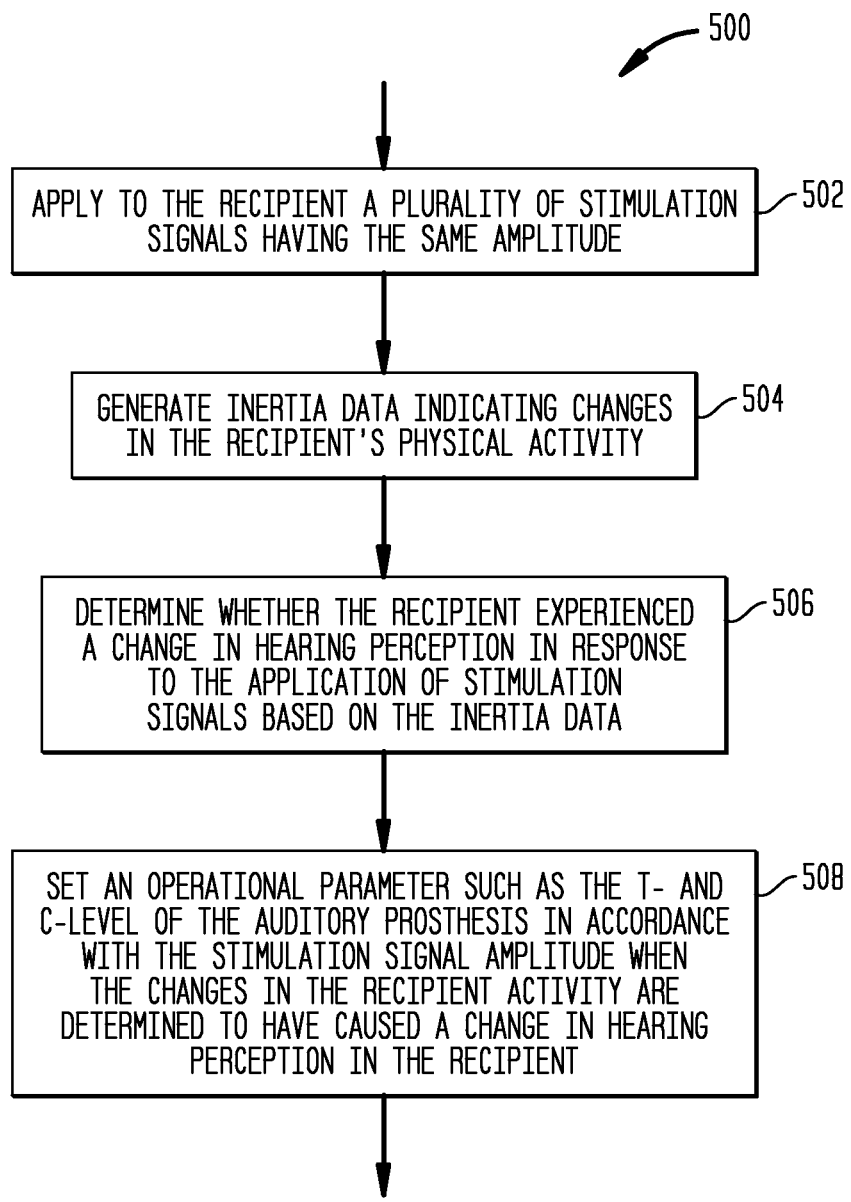

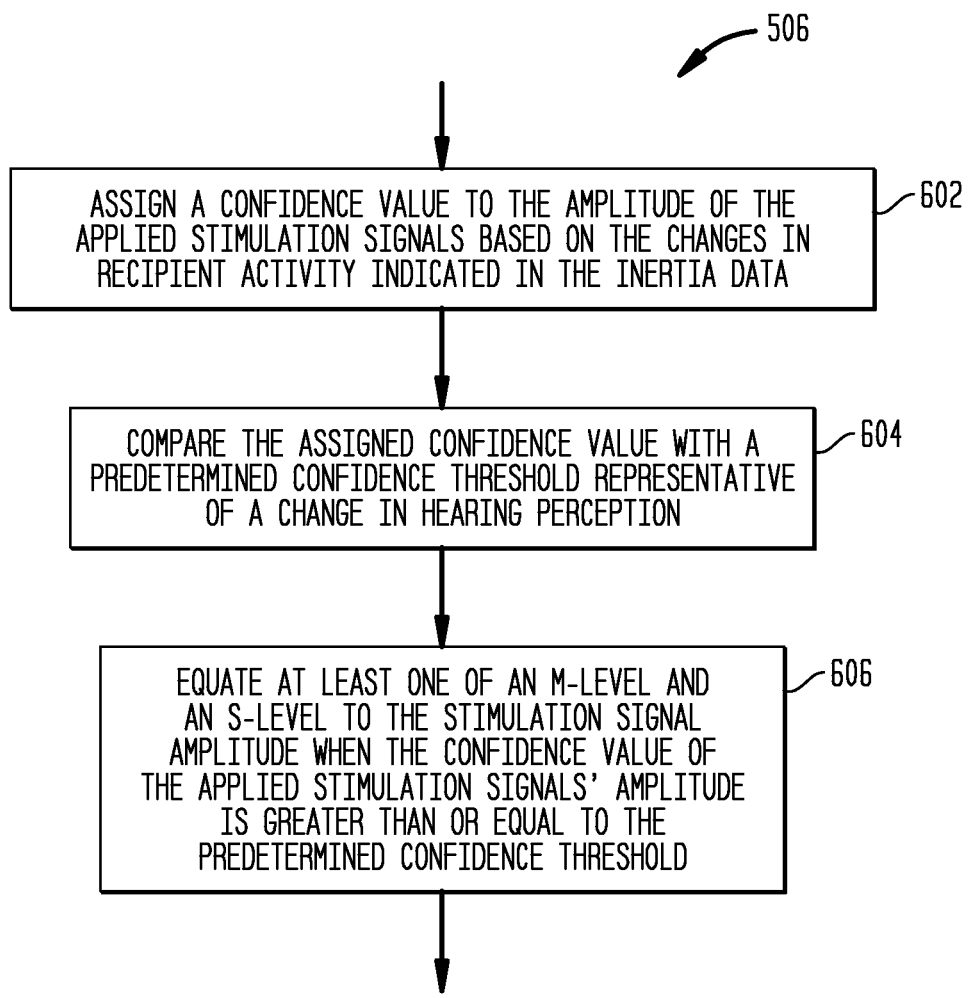

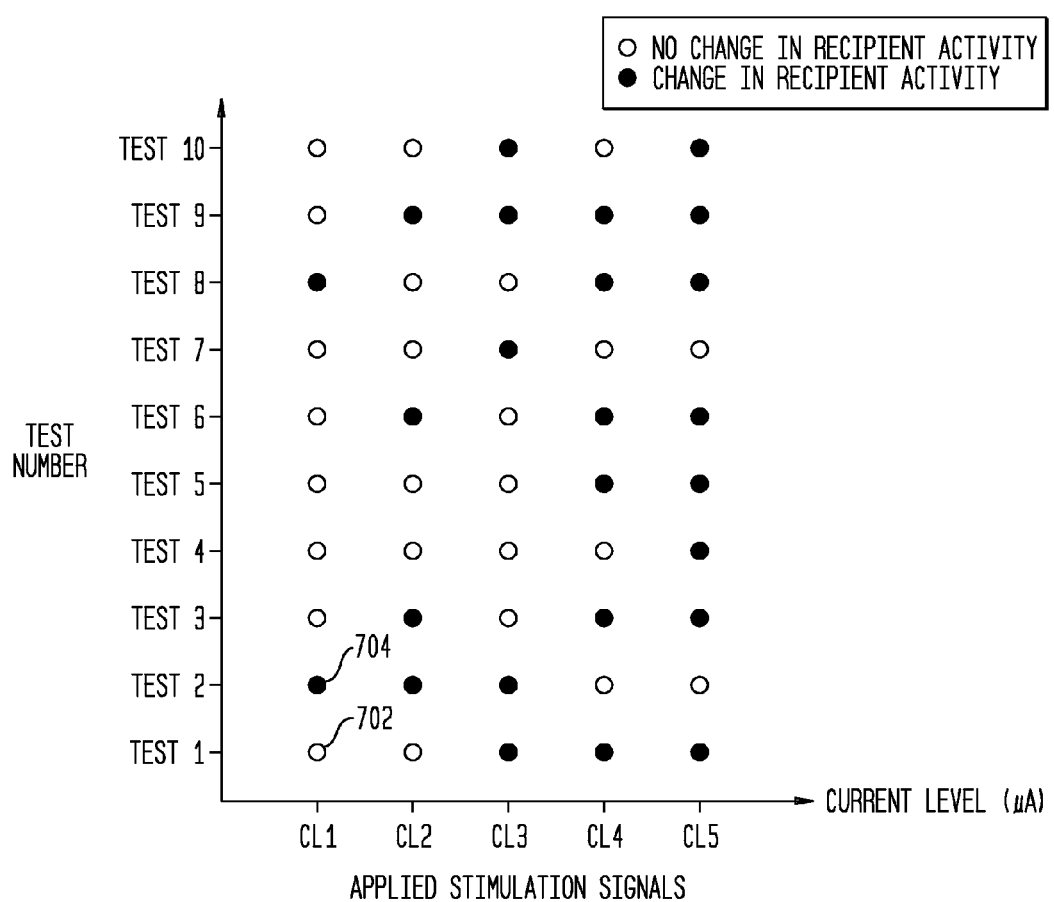

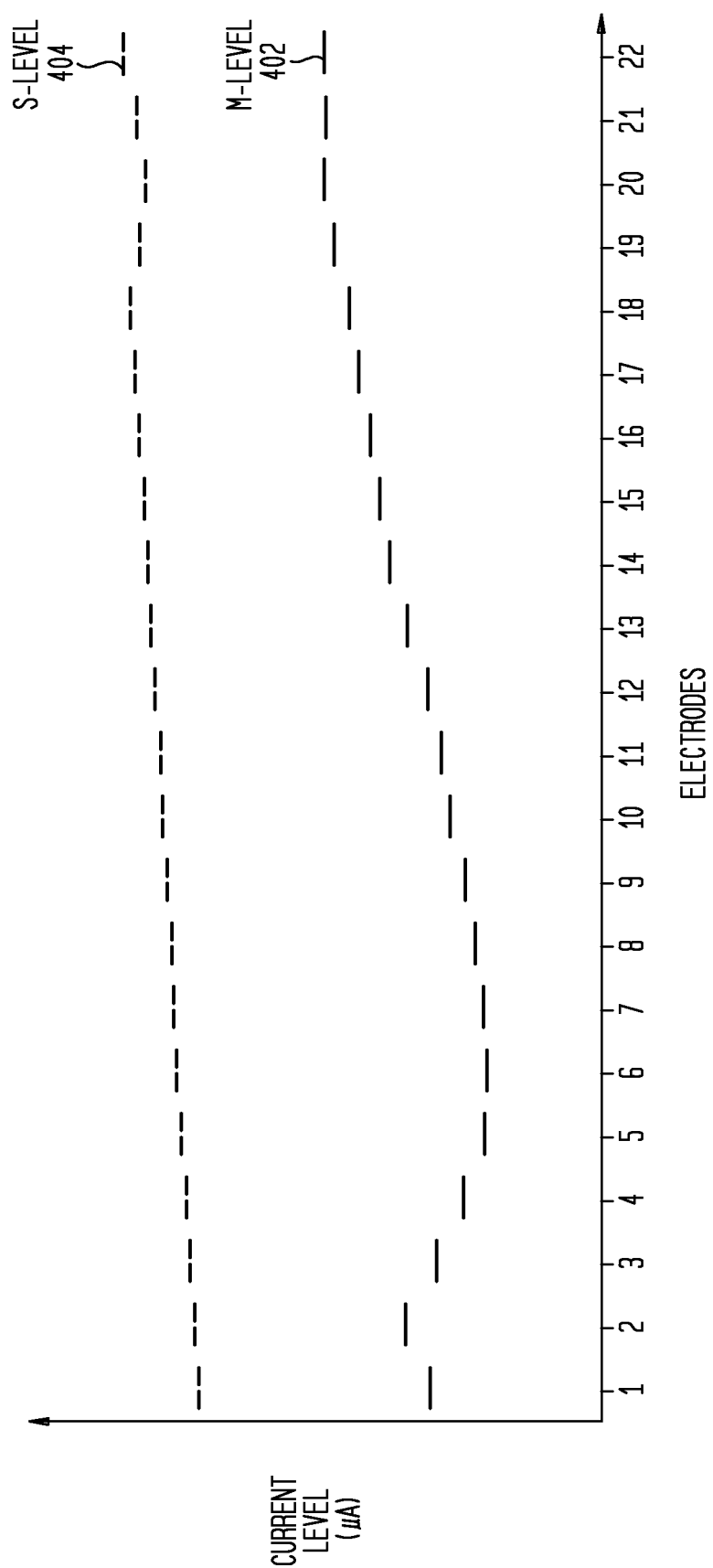

METHOD AND DEVICE FOR AUTOMATED OBSERVATION FITTING

CROSS-REFERENCE TO RELATED APPLICATIONS

The present application claims priority from U.S. Provisional Patent Application 60/798,312, entitled "Method and Device For Automated Observational Fitting" filed on May 8, 2006, which is hereby incorporated by reference herein.

BACKGROUND

1. Field of the Invention

The present invention relates generally to auditory prostheses and, more particularly, to automated fitting of an auditory prosthesis to a recipient.

2. Related Art

Hearing loss, which may be due to many different causes, is generally of two types, conductive and sensorineural. In some cases, a person may have hearing loss of both types. Conductive hearing loss occurs when the normal mechanical pathways that provide sound to hair cells in the cochlea are impeded due to, for example, damage to the ossicles. Conductive hearing loss is often addressed with conventional hearing aids which amplify sound.

On the other hand, sensorineural hearing loss is due to the absence or destruction of the cochlear hair cells which transduce acoustic signals into nerve impulses. Those suffering from sensorineural hearing loss are thus unable to derive suitable benefit from conventional hearing aids. As a result, stimulating auditory prostheses have been developed to provide persons having sensorineural hearing loss with the ability to perceive sound. Such auditory prostheses include, for example, auditory brain stimulators and cochlear™ prostheses (commonly referred to as cochlear™ prosthetic devices, cochlear™ implants, cochlear™ devices, and the like; simply "cochlea implants" herein.)

Cochlear implants use direct electrical stimulation of auditory nerve cells to bypass absent or defective hair cells that normally transduce acoustic vibrations into neural activity. Such devices generally use an electrode array implanted into the scala tympani of the cochlea so that the electrodes may differentially activate auditory neurons that normally encode differential pitches of sound. Auditory brain stimulators are used to treat a smaller number of recipients with bilateral degeneration of the auditory nerve. For such recipients, the auditory brain stimulator provides stimulation of the cochlear nucleus in the brainstem.

Typically, following the surgical implantation of a cochlear implant, the recipient must have the implant fitted or customized to conform to the specific physiology of that recipient. This procedure is often referred to as "programming," "mapping" or "fitting" ("fitting" herein). Fitting an auditory prosthesis involves measuring and controlling the amount of electrical current delivered by the cochlea implant to provide comfortable and usable stimulation to the recipient. To do so, the fitting process involves the collection and determination of recipient-specific parameters such as threshold levels (T-levels) and comfort levels (C-levels) for each stimulation channel. This collection of recipient-specific parameters for each of a plurality of stimulation channels is commonly referred to as a "program" or "map" ("MAP" herein). The implementation of the MAP ensures that the stimulation from the cochlear implant provides a recipient with comfortable and accurate auditory perception, enabling the recipient to receive maximum benefit from the device.

Essentially, an audiologist or clinician performs what is commonly referred to as psychophysics measurements by applying stimulation pulses for each channel and subjectively interpreting a behavioral indication from the implant recipient as to the threshold and comfort levels of the perceived sound. For implants with a large number of stimulation channels this process is quite time consuming for the audiologist and relies heavily on the recipient's subjective impression of the stimulation. Also, the psychophysics approach is further limited in the cases of children, infants and prelingually or congenitally deaf recipients who are unable to provide an accurate impression of the resultant hearing sensation. Hence the fitting of the implant may be sub-optimal and may directly hamper the speech and hearing development of younger recipients.

SUMMARY

In accordance with one aspect of the present invention, a method for fitting an auditory prosthesis to a recipient is disclosed, the method comprising: applying at least one stimulation signal to the recipient; generating inertia data indicating changes in the recipient's physical activity; and determining whether the recipient experienced a change in hearing perception in response to the stimulation signal based on the inertia data.

In accordance with another aspect of the present invention, a method for fitting an auditory prosthesis to a recipient is disclosed, the method comprising: detecting changes in recipient activity with an inertial measurement unit; and automatically determining operational thresholds of the prosthesis based on the detected changes in recipient activity that occur in response to applied stimulation signals.

In accordance with another aspect of the present invention, a system for providing operational parameters to a fitting system of an auditory prosthesis of a recipient is disclosed, the system comprising: an inertial measurement unit constructed and arranged to generate inertia data indicating changes in the recipient's physical activity; and a determinator configured to determine whether the recipient experienced a change in hearing perception in response to applied stimulation signals based on the inertia data.

In accordance with a further aspect of the present invention, a system for automatically determining operational parameters of an auditory prosthesis for a recipient is disclosed, the system comprising: an apparatus configured to cause the auditory prosthesis to apply stimulation signals to the recipient; an inertial measurement unit configured to generate inertia data indicating changes in the recipient's physical activity; and a determinator configured to determine whether the recipient experienced a change in hearing perception in response to the stimulation signals based on the inertia data.

BRIEF DESCRIPTION OF THE DRAWINGS

Embodiments of the invention are described below in conjunction with the accompanying drawings, in which:

FIG. 1A is a perspective view of an exemplary auditory prosthesis and associated fitting system in which embodiments of the present invention may be advantageously implemented;

FIG. 1B is a schematic diagram illustrating a auditory prosthesis fitting arrangement in which embodiments of the present invention may be advantageously implemented;

FIG. 3E is the high-level block diagram of the cochlear implant illustrated in FIG. 1A in which the components of an embodiment of the present invention illustrated in FIG. 2A are implemented, in accordance with one embodiment of the present invention;

FIG. 5 is a high-level flow chart of the operations performed by embodiments of the present invention in conjunction with a fitting system of the auditory prosthesis;

FIG. 6 is a high-level flow chart of the operations performed by embodiments of the present invention in conjunction with a fitting system of the auditory prosthesis;

FIG. 7A is a graph illustrating the recipient's response to the repetitive application of various stimulation signals;

FIG. 9A illustrates the determination of M- and S-levels for individual electrodes.

DETAILED DESCRIPTION

Figure 2A:
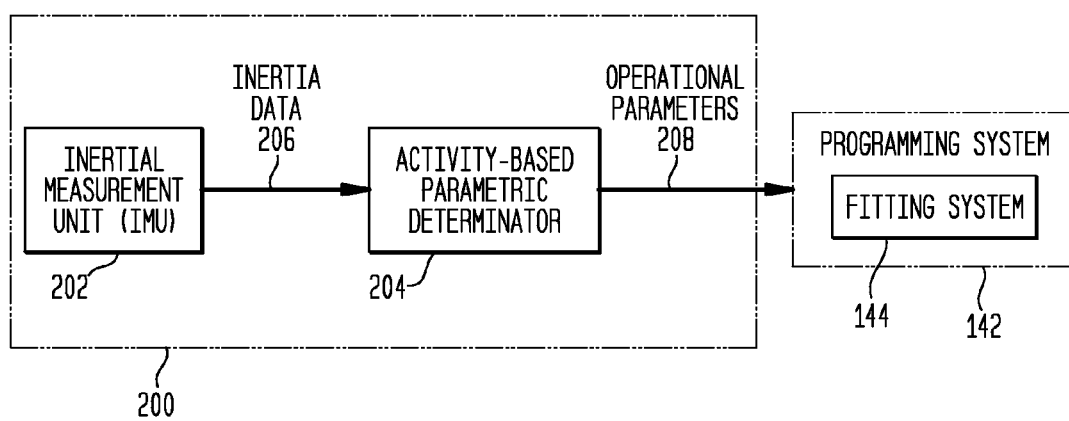
FIG. 2A is a high-level block diagram of one embodiment of the present invention.

Aspects of the present invention relate generally to fitting an auditory prosthesis to a recipient. Embodiments of the invention automatically determine operational thresholds of the prosthesis based on changes in the activity of the recipient that occur in response to applied stimulation signals. Such changes in recipient activity are detected by an inertial measurement unit (IMU) permanently or temporarily secured to or implanted in the recipient as an integral part of the prosthesis or a separate device operationally coupled to the prosthesis.

Embodiments of the present invention may be implemented in conjunction with a variety of auditory prostheses commercially available today or developed in the future. For ease of illustration, embodiments of the present invention are described herein in conjunction with the fitting of one particular type of auditory prosthesis, a cochlear implant.

Although the present invention may be implemented to facilitate the fitting of an auditory prosthesis to any type of patient, the present invention provides particular benefits when fitting an auditory prosthesis to children, infants and prelingually or congenitally deaf recipients who are unable to provide an audiologist with an accurate impression of the hearing sensation resulting from an applied stimulation signal. Accordingly, embodiments of the present invention are described herein in conjunction with the fitting of a cochlear implant to one particular recipient, a child.

FIG. 1A is a perspective view of a cochlear implant 100 implanted in a recipient. The relevant components of the recipient's outer ear 101, middle ear 105 and inner ear 107 are described next below, followed by a description of cochlear implant 100.

An acoustic pressure or sound wave 103 is collected by auricle 109 and channeled into and through ear canal 102. Disposed across the distal end of ear canal 102 is a tympanic membrane 104 which vibrates in response to acoustic wave 103.

This vibration is coupled to oval window or fenestra ovalis 115 through three bones of middle ear 105, collectively referred to as the ossicles 117 and comprising the malleus 113, the incus 109 and the stapes 111. Bones 113, 109 and 111 of middle ear 105 serve to filter and amplify acoustic wave 103, causing oval window 115 to articulate, or vibrate. Such vibration sets up waves of fluid motion within cochlea 132. Such fluid motion, in turn, activates tiny hair cells (not shown) that line the inside of cochlea 132. Activation of the hair cells causes appropriate nerve impulses to be transferred through the spiral ganglion cells (not shown) and auditory nerve 138 to the brain (not shown), where they are perceived as sound.

Cochlear implant 100 comprises external component assembly 142 which is directly or indirectly attached to the body of the recipient, and an internal component assembly 144 which is temporarily or permanently implanted in the recipient.

External assembly 142 comprises a sound processing unit 116 and an external transmitter unit 106. Sound processing unit 116 typically includes a digital signal processor (DSP), a power source to power cochlear implant 100, and a sound transducer 120. Sound transducer 120 detects sound and generates an audio signal, typically an analog audio signal, representative of the detected sound. In this illustrative embodiment, sound transducer 120 is a microphone. In alternative embodiments, sound transducer 120 may comprise, for example, more than one microphone, one or more telecoil induction pickup coils or other devices now or later developed that may detect sound and generate electrical signals representative of such sound. In some embodiments, sound transducer 120 is not integrated into sound processing unit 116 but rather is a separate component of external component assembly 142.

External transmitter unit 106 comprises an external coil 108 of a transcutaneous energy transfer system along with the associated circuitry to drive the coil. External transmitter unit 106 also preferably comprises a magnet (not shown) secured directly or indirectly to the external coil 108.

Sound processing unit 116 processes the output of microphone 120 that is positioned, in the depicted embodiment, by auricle 109 of the recipient. Sound processing unit 116 generates coded signals, referred to herein as stimulation data signals, which are provided to external transmitter unit 106 via a cable (not shown). Sound processing unit 116 is, in this illustration, constructed and arranged so that it can fit behind auricle 109. Alternative versions may be worn on the body or it may be possible to provide a fully implantable system which incorporates the sound processing unit into the internal component assembly 144.

Internal component assembly 144 comprises an internal receiver unit 112, a stimulator unit 126 and an electrode assembly 118. Internal receiver unit 112 and stimulator unit 126 are hermetically sealed within a biocompatible housing.

Internal receiver unit 112 comprises an internal coil (not shown) of the noted transcutaneous transfer system, along with the associated circuitry. When implanted internal receiver unit 112 may be positioned in a recess of the temporal bone adjacent to outer ear 101 of the recipient, as shown in FIG. 1A. External coil 108 may be held in place aligned with the implanted internal coil via the noted magnets. In one embodiment, external coil 108 transmits electrical signals to the internal coil via a radio frequency (RF) link.

Electrode assembly 118 extends from stimulator unit 126 to cochlea 132 and terminates in an array 134 of electrodes 136. Signals generated by stimulator unit 126 are applied by electrodes 136 to cochlea 132, thereby stimulating auditory nerve 138.

Further details of the above and other exemplary cochlear implants which may be implemented in conjunction with embodiments of the present invention include, but are not limited to, those systems described in U.S. Pat. Nos. 4,532,930, 6,537,200, 6,565,503, 6,575,894 and 6,697,674, which are hereby incorporated by reference herein in their entireties. It should be appreciated that other embodiments of the present invention may be implemented in conjunction with other stimulating auditory prostheses as well as other types of auditory prostheses such as middle ear implants which deliver mechanical stimulation signals, and hearing aids, which deliver acoustic stimulation signals.

As shown in FIG. 1A, cochlear implant 100 is further configured to interoperate with an external programming system 142 such as a personal computer, workstation or the like, implementing an auditory prosthesis fitting system 143. This is described in greater detail below with reference to an exemplary fitting environment illustrated in FIG. 1B.

The effectiveness of an auditory prosthesis depends not only on the device itself but also on how well the device is configured or "fit" for the recipient. Fitting of an auditory prosthesis, also referred to as "programming" or "mapping," creates a set of instructions and data that defines the specific characteristics of the stimulation signal delivered to the electrodes 136 of the implanted array 134. As noted, this collection of information is referred to as the recipient's "program" or "MAP." FIG. 1B is a schematic diagram illustrating one exemplary arrangement 150 in which a fitting system 144 is utilized to fit cochlear implant 100 to a recipient 162.

As shown in FIG. 1B, an audiologist or clinician 164 uses an auditory prosthesis fitting system 144 ("fitting system" herein) comprising interactive software and computer hardware to create individualized recipient map data 182 that are digitally stored on system 144 and ultimately downloaded to the memory of sound processor unit 116 (FIG. 1A) for recipient 162. System 144 is programmed and/or implements software programmed to carry out one or more of the functions of mapping, neural response measuring, acoustic stimulating 172, and interfacing with embodiments of the present invention to receive automatically-determined operational parameters. Alternatively, fitting system 144 may be configured to include elements of the present invention to which automatically-determine the operational parameters.

In the embodiment illustrated in FIG. 1B, sound processing unit 116 of cochlear implant 100 is connected directly to fitting system 144 to establish a data communication link 168 between the speech processor and fitting system. System 144 is thereafter bi-directionally coupled with sound processor unit 116 by means of data communication link 168. It should be appreciated that although sound processor unit 116 and fitting system 144 are connected via a cable in FIG. 1B, any communications link now or later developed may be utilized to communicably couple these components.

Once cochlear implant 100 is calibrated, specific mapping data 182 is determined. The particular details of the implemented fitting process are specific to the recipient, cochlear implant manufacturer, cochlear implant device, etc. As a result, only selected exemplary mapping data are described herein for clarity.

Today, most cochlear implants require at least two values to be set for each stimulating electrode 136. These values are referred to as the Threshold level (commonly referred to as the "THR" or "T-level;" "threshold level" herein) and the Maximum Comfortable Loudness level (commonly referred to as the Most Comfortable Loudness level, "C-level;" simply "comfort level" herein). Threshold levels (T levels) and maximum comfort levels (C levels) vary from recipient to recipient and from stimulation channel to stimulation channel and are essential in determining how well the recipient hears and understands detected speech or sound.

The T level is defined as the level at which the recipient first identifies sound sensation, and is the lowest level of stimulation that evokes the sensation of sound for a given channel. The T level is often determined by passing the recipient's hearing threshold twice using an ascending method and determining the level at which the recipient experiences sound by observing their response by indicating gestures in the case of adults, or behavioral reactions in the case of children.

The C level sets the maximal allowable stimulation level for each electrode channel and is defined as the maximal stimulation level that feels comfortable to the recipient. In setting and establishing the C levels, it is usual to instruct the recipient to indicate a level which is "as loud as would be comfortable for long periods" whilst slowly increasing the stimulation. The C levels affect how speech sounds to the recipient more than T levels as most of the acoustic speech signal will be mapped onto the top 20% of the T and C level range.

It should be appreciated that although the terminology and abbreviations are device-specific, the general purpose of threshold and comfort levels is common among all cochlear implants: to determine a recipient's electrical dynamic range.

In adult cochlear implant patients, threshold and comfort levels are typically measured using verbal feedback from recipient 162. For children, who often lack the listening experience, language, or conceptual development to perform specific fitting tasks, audiologists and clinicians have traditionally relied on clinical intuition and trial and error to appropriately estimate comfort levels for young recipients. As will be described in detail below, such fitting tasks may be substituted or supplemented with automatically-determined parametric values in accordance with the teachings of the present invention.

The above and other feedback is generally referred to by reference numeral 184, while the automatically determined parametric values, or inertial measurement data used to make such determinations (described below), are included in performance data 180B. Performance data provided directly to fitting system 144 may be provided via a data connection 168 as performance data 180B, while performance data provided by the audiologist/clinician based on oral feedback or observations 184 is shown in FIG. 1B as performance data 180A (performance data 180A and 180B are generally and collectively referred to herein as performance data 180).

As noted, in this exemplary application, recipient 162 is a child and, as such, the development of MAP data 182 is difficult, time consuming, and the resulting data is often inaccurate. Implementation of the present invention provides for an automated fitting procedure of cochlear implant 100, which is based on behavioral responses of recipient 162. Instead of or in addition to having an audiologist observe 184 the child's behavior and inputting such observations into the auditory prosthesis fitting system 144 (as performance data 180A). Embodiments of the present invention detect and measure the degree of change of activity of the recipient in response to applied stimulation signals, and automatically determine operational parameters such as T- and C-levels for cochlear implant 100.

FIG. 2A is a high-level block diagram of one embodiment of the present invention. System 200 comprises an inertial measurement unit (IMU) 202 constructed and arranged to measure the inertia, that is, changes in physical activity, of recipient 162. IMU 202 is further configured to provide inertia data 206 to an activity-based parametric determinator 204 configured to determine operational parameters based on the inertia data.

Figure 2B:
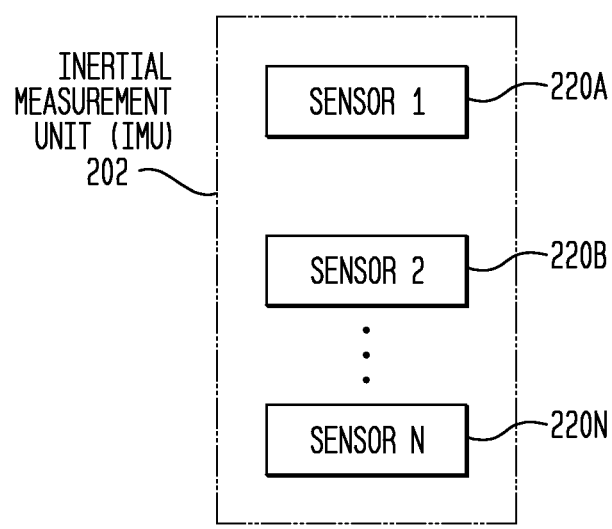
FIG. 2B is a block diagram of an inertial measurement unit (IMU) in accordance with one embodiment of the present invention.

Referring to FIG. 2B, IMU 202 may comprise one or more sensors 220 each configured to sense rectilinear or rotatory motion, or both, in the same or different axes. Examples of sensors 220 which may comprise IMU 202 include accelerometers, gyroscopes, compasses, and the like. Such sensors may be implemented in, for example, MEMS (micro electromechanical systems) or with other technology suitable for the particular application. In one embodiment, IMU 202 has a box-like shape with dimensions less than or equal to 5 mm×5 mm×5 mm. In another embodiment, IMU 200 comprises four sensors: three single axis gyroscopes 220A-C and a three-axis accelerometer 220D, as described in Benbasat A. Y. and Paradiso J. A., An Inertial Measurement Framework For Gesture Recognition And Applications, Wachsmuth and T. Sowa (Eds.): GW 2001, LNAI 2298, pp. 9-20, 2002, which is hereby incorporated by reference herein. The activity data 206 generated by IMU 202 comprises acceleration data in three or more measured axes. The IMU sensors generate such data continuously which, as noted, is provided to determinator 204.

Determinator 204 measures inertia data 206 to determine whether there were changes in recipient activity in response to the application of a plurality of stimulation signals which indicate that the recipient made such changes in activity in response to a hearing perception. In one embodiment, described below, such a determination may be made by assigning confidence values to each response for a statistically relevant quantity of test events. Determinator 204 then compares the summation of such confidence values with a predetermined threshold indicative of a hearing perception. It should be appreciated that in alternative embodiments determinator 204 may implement other techniques such as correlation and pattern recognition functions.

Figure 3:
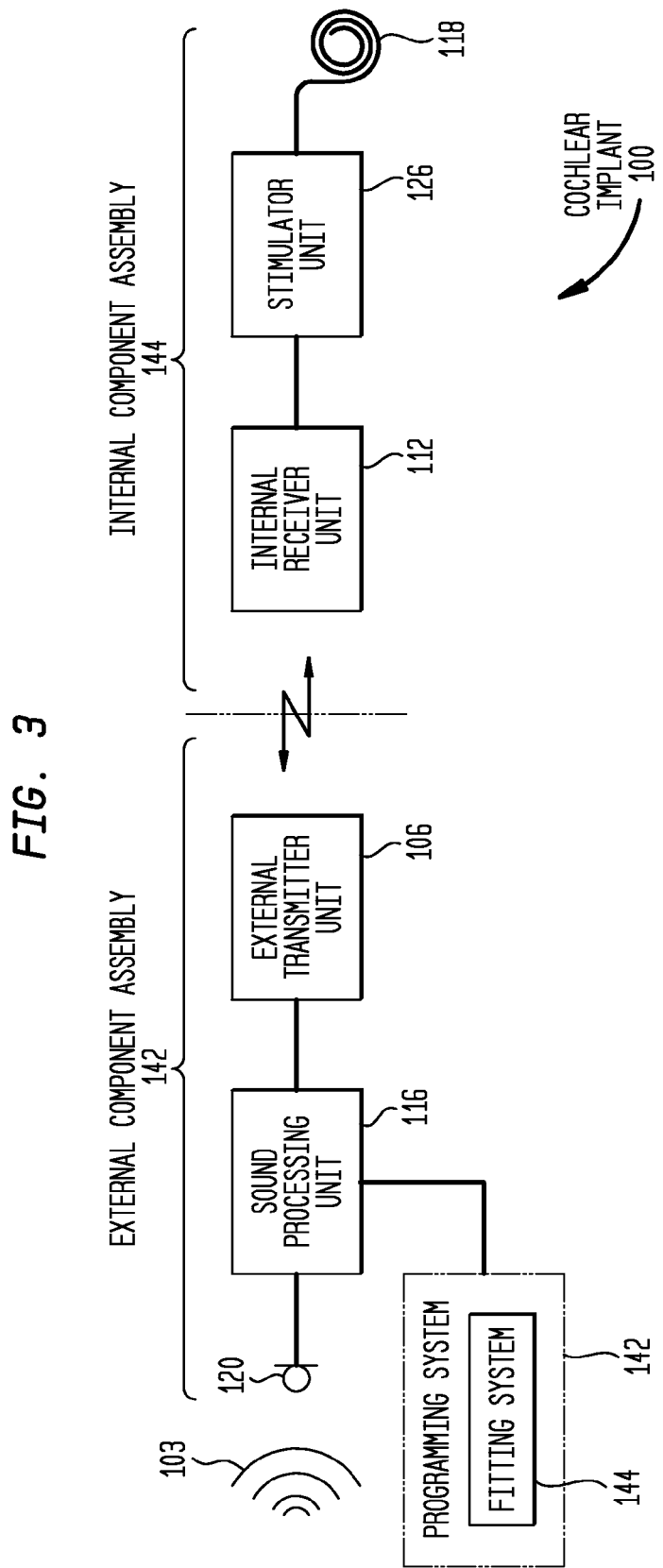
FIG. 3 is a high-level block diagram of the cochlear implant illustrated in FIG. 1A.

IMU 202 and determinator 204 may be implemented in a variety of locations in conjunction with cochlear implant 100 and fitting system 144. Embodiments of cochlear implant 100 and programming system 142 implementing various embodiments of the present invention are described next below with reference to FIGS. 3A-3F. To facilitate this description, a simplified block diagram of cochlear implant 100 is depicted in FIG. 3 and described next below.

Cochlear implant 100 comprises external component assembly 142 and internal component assembly 144. External assembly 142 comprises microphone 120, sound processing unit 116 and external transmitter unit 106. Internal component assembly 144 comprises internal transmitter unit 112, stimulator unit 126 and electrode assembly 118. These components are configured as described above to receive and process sound 103 to generate representative stimulation signals delivered to cochlea 132 (FIG. 1A) via electrode assembly 118.

Figure 3A:
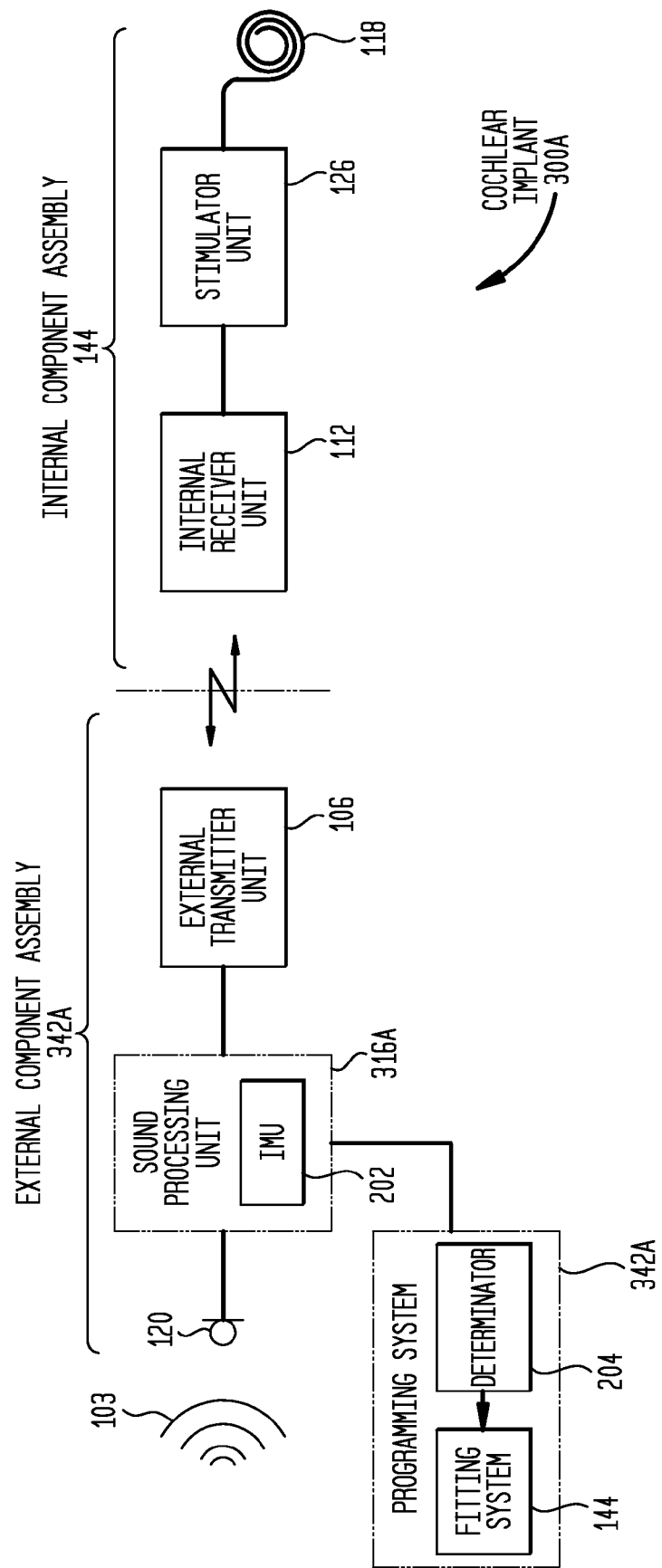
FIG. 3A is the high-level block diagram of the cochlear implant illustrated in FIG. 1A in which the components of an embodiment of the present invention illustrated in FIG. 2A are implemented, in accordance with one embodiment of the present invention.

FIGS. 3A-3F are exemplary embodiments of system 200 implemented in various components of cochlear implant 100 and/or programming system 142. In FIG. 3A, a cochlear implant 300A comprises an external component assembly 342A due to the integration of IMU 202 into sound processing unit 116, referred to herein as sound processing unit 316A. In this exemplary embodiment, determinator 204 is implemented in programming system 142, referred to herein as programming system 342A. In one such embodiment, IMU 202 provides inertia data 206 to determinator 204 via communication link 168. In one such embodiment, operational parameters 208 are provided by determinator 204 to fitting system 144 via a direct software connection.

Figure 3B:
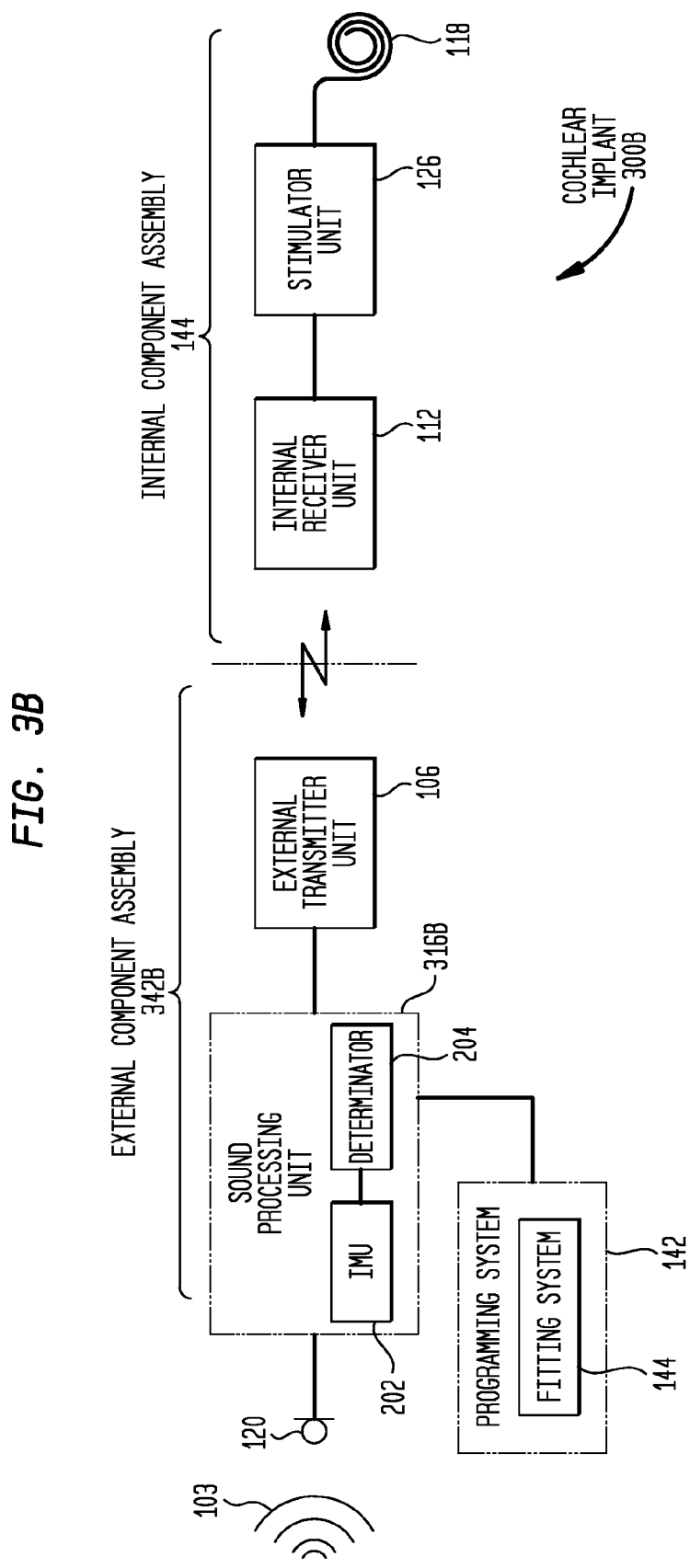
FIG. 3B is the high-level block diagram of the cochlear implant illustrated in FIG. 1A in which the components of an embodiment of the present invention illustrated in FIG. 2A are implemented, in accordance with one embodiment of the present invention.

In FIG. 3B, a cochlear implant 300B comprises an external component assembly 342A due to the integration of IMU 202 and determinator 204 into sound processing unit 116, referred to herein as sound processing unit 316B. In one such embodiment, IMU 202 provides inertia data 206 to determinator 204 via a direct hardware/software communication link. In one such embodiment, operational parameters 208 are provided by determinator 204 to fitting system 144 via communication data link 168 (FIG. 1B) provided between programming system 142 and cochlear implant 300B.

Figure 3C:
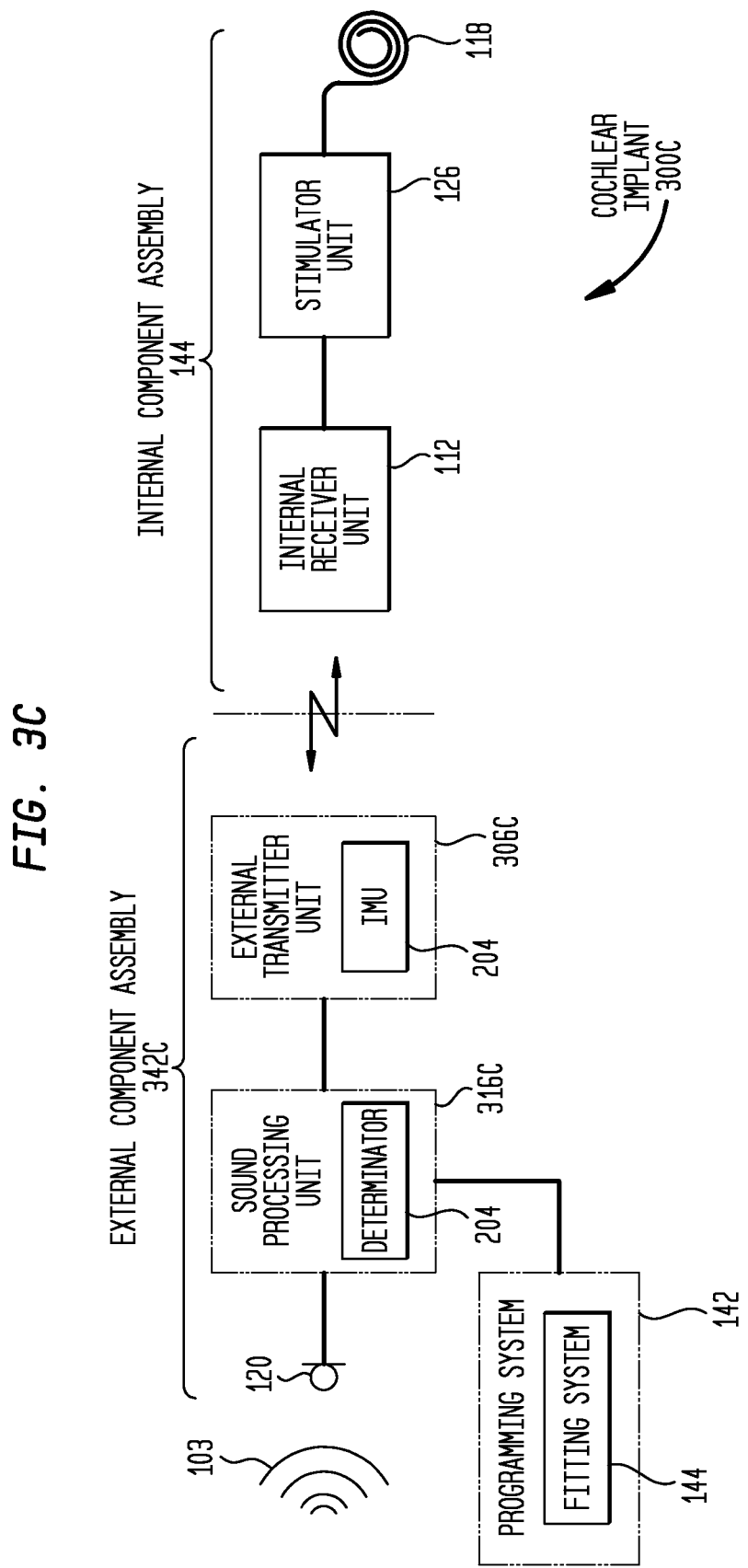
FIG. 3C is the high-level block diagram of the cochlear implant illustrated in FIG. 1A in which the components of an embodiment of the present invention illustrated in FIG. 2A are implemented, in accordance with one embodiment of the present invention.

In FIG. 3C, a cochlear implant 300C comprises an external component assembly 342A due to the integration of IMU 202 into external transmitter unit 106, referred to herein as external transmitter unit 306C, and the integration of determinator 204 into sound processing unit 116, referred to herein as sound processing unit 316C. In one such embodiment, IMU 202 provides inertia data 206 to determinator 204 via the data line connecting external transmitter 306C and sound processing unit 316C. In one such embodiment, operational parameters 208 are provided by determinator 204 to fitting system 144 via communication data link 168 (FIG. 1B) provided between programming system 142 and cochlear implant 300C.

Figure 3D:
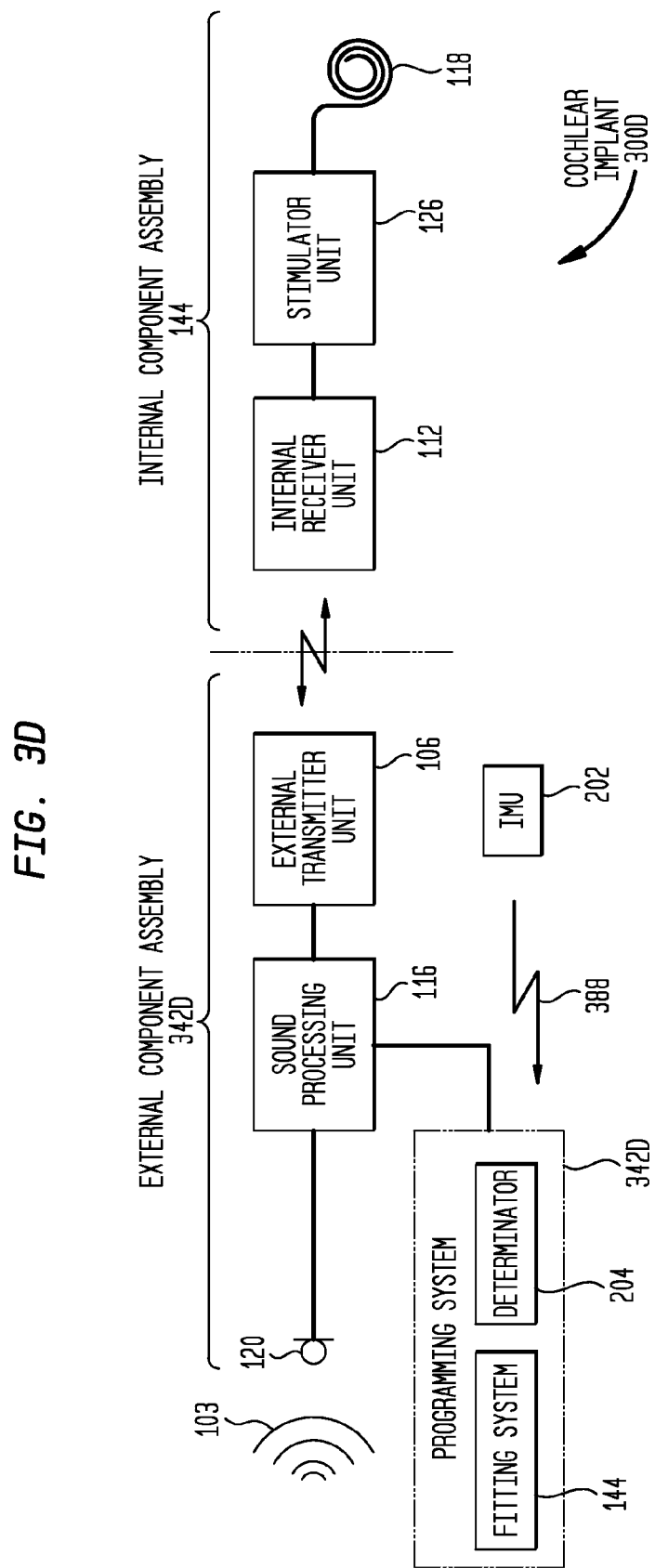
FIG. 3D is the high-level block diagram of the cochlear implant illustrated in FIG. 1A in which the components of an embodiment of the present invention illustrated in FIG. 2A are implemented, in accordance with one embodiment of the present invention.

In FIG. 3D, a cochlear implant 300D comprises an external component assembly 342D due to the implementation of IMU 202 elsewhere on recipient 162 other than in external transmitter unit 106 or sound processing unit 116. In embodiments in which IMU 200 is an external device, sensor(s) 220 of IMU 202 may be worn by or attached to recipient 162 in the form of a band around the arm, neck, waist, leg or head, or securely attached to the body or head with appropriate sutures, glue, etc.

In this embodiment, determinator 204 is implemented in programming system 142, referred to herein as programming system 342D. In one such embodiment, IMU 202 provides inertia data 206 to determinator 204 via a wireless connection such as a radio-frequency (RF) link, represented by arrow 388. In one such embodiment, operational parameters 208 are provided by determinator 204 to fitting system 144 via a direct software connection.

In FIG. 3E, a cochlear implant 300E comprises an internal component assembly 344E due to the integration of IMU 202 into stimulator unit 126, referred to herein as stimulator unit 326E. Cochlear implant 300E further comprises external component assembly 342E due to the integration of determinator 204 in sound processing unit 116, referred to herein as sound processing unit 316E. In one such embodiment, IMU 202 provides inertia data 206 to determinator 204 via the transcutaneous data link established between internal receiver unit 112 and external transmitter unit 106. Due to the continuous generate of inertia data 206, in some embodiments a separate IR data link is provided for communications between IMU 202 and an IR received integrated into external transmitter unit 106. The received inertia data 206 is then provided to determinator 204 via the data line connecting external transmitter unit 106 and sound processing unit 316E. In one such embodiment, operational parameters 208 are provided by determinator 204 to fitting system 144 via communication data link 168 (FIG. 1B) provided between programming system 142 and cochlear implant 300E.

Figure 3F:
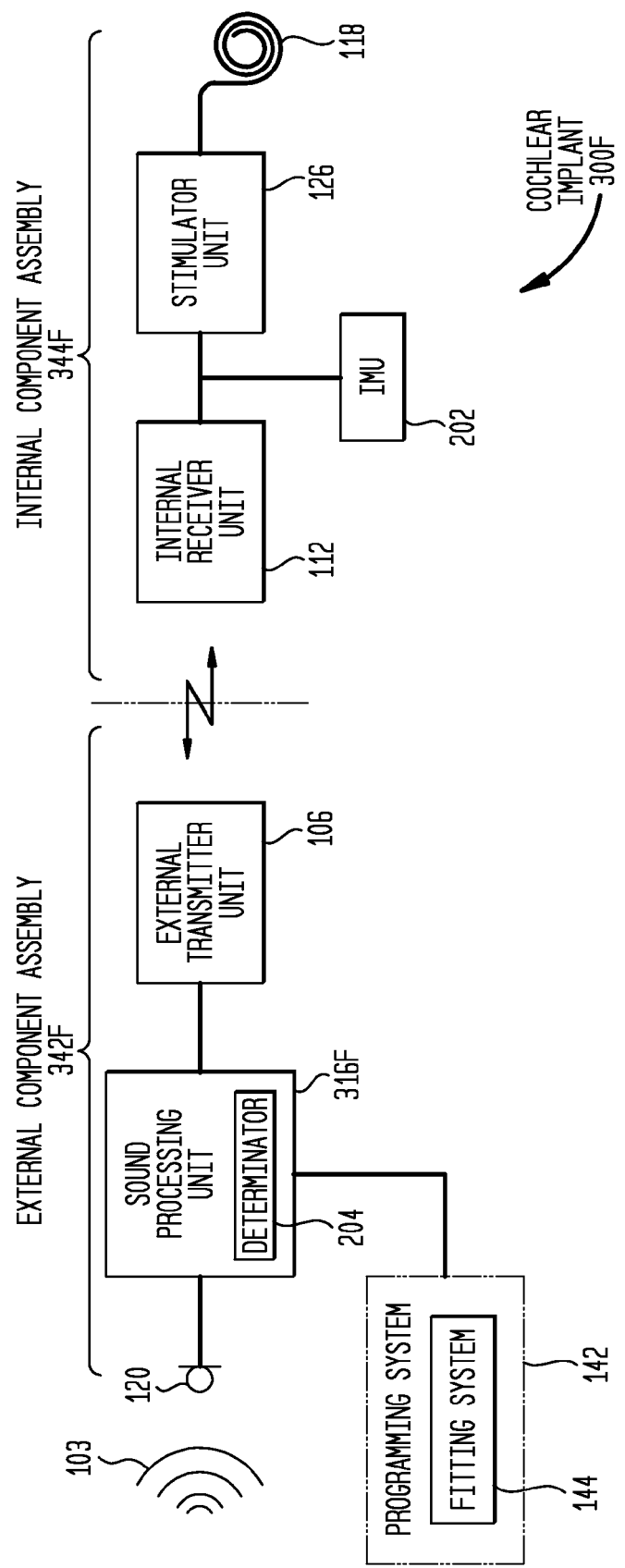
FIG. 3F is the high-level block diagram of the cochlear implant illustrated in FIG. 1A in which the components of an embodiment of the present invention illustrated in FIG. 2A are implemented, in accordance with one embodiment of the present invention.

In FIG. 3F, a cochlear implant 300F comprises an internal component assembly 344F due to the implantation of IMU 202 into recipient 162. In contrast to the above or other embodiments in which sensors 220 of IMU 202 are integrated into a component of internal component assembly 144, in embodiments represented by FIG. 3F, sensor(s) 220 are implanted in recipient 162. In one embodiment, sensor(s) 220 are implanted in the subcutaneous tissue beneath the skin of recipient 162 so that they may easily be removed. In alternative embodiments, sensor(s) 220 are secured to different locations on the skull.

Cochlear implant 300F further comprises external component assembly 342F due to the integration of determinator 204 in sound processing unit 116, referred to herein as sound processing unit 316E. In one such embodiment, IMU 202 provides inertia data 206 to determinator 204 via the transcutaneous data link or an IR data link, as noted above. The received inertia data 206 is then provided to determinator 204 via the data line connecting external transmitter unit 106 and sound processing unit 316E. In one such embodiment, operational parameters 208 are provided by determinator 204 to fitting system 144 via communication data link 168 (FIG. 1B) provided between programming system 142 and cochlear implant 300F.

It should be appreciated that the embodiments illustrated in FIGS. 3A-3F are exemplary only and that IMU 202 and determinator 204 may be implemented in other components or combination of components that those presented above. Also, as noted above with reference to FIG. 2B, IMU 202 may comprise a series of sensors 220 which may be configured to attach to a variety of locations in and/or on recipient 162 to obtain accurate inertia measurements of recipient 162. In certain embodiments in which sensors 220 are located within recipient 162, termometers are included to compensate for drift caused by temperature variations.

Depending on where the IMU device is located on the body of child recipient 162, other subtle movements may be measured and used in the automated fitting procedure of the present invention. These include, but are not limited to, head-movement, eye-movement, breathing rhythm, arm and leg movements, eating, drinking, grabbing hands, etc. Sensors 220 of a second IMU 202 may be attached to objects in the child recipient's environment, such as toys. Such multiple IMU devices may be used and combined. As noted, the present invention may be implemented to compliment other fitting procedures conducted by audiologist/clinician 164. In such application, operational parameters 206 generated by system 200 may be processed in fitting system 144 in combination with data from other sources such as a GPS device carried by the recipient, a video camera, a sound recorder, and the like.

It should also be appreciated that the functions and operations of determinator 204 may be implemented in hardware, software or a combination thereof. Although determinator 204 is depicted in FIGS. 3A-3F as a single functional element, it should be appreciated that such a depiction is for simplicity only, and that the functions performed by determinator 204 may be distributed across a number of elements which may be located in the same component of cochlear implant 100, or distributed across a number of components of cochlear implant 100.

According to one embodiment of the present invention, after implantation of the cochlear implant 100, the child receives sound processor 116 with default settings. Because all T-level and C-level values are set to zero, sound processor 116 performs sound processing operations with cochlear implant 100 generating no stimulation signals. To automatically determine the T- and C-levels based on inertia data 206 generated by IMU 200, two new levels are introduced: the M-Level and the S-Level. The M-level for a given electrode channel or frequency band is defined as the current level of an electrical stimulation that causes the recipient, such as a child, who was standing still to suddenly start moving, because he/she probably experienced a hearing perception. The stimulation level which results in the initiation of activity, or movement, is referred to herein as an M-level. Conversely, the S-level for a given electrode channel or frequency band is defined as the current level of an electrical stimulation signal that causes the child recipient which was in motion when the stimulation signal was applied, to suddenly cease such movement, because he/she probably experienced a hearing perception. The stimulation level which results in the cessation of movement is referred to herein as the stop level, or S-level.

Figure 4:
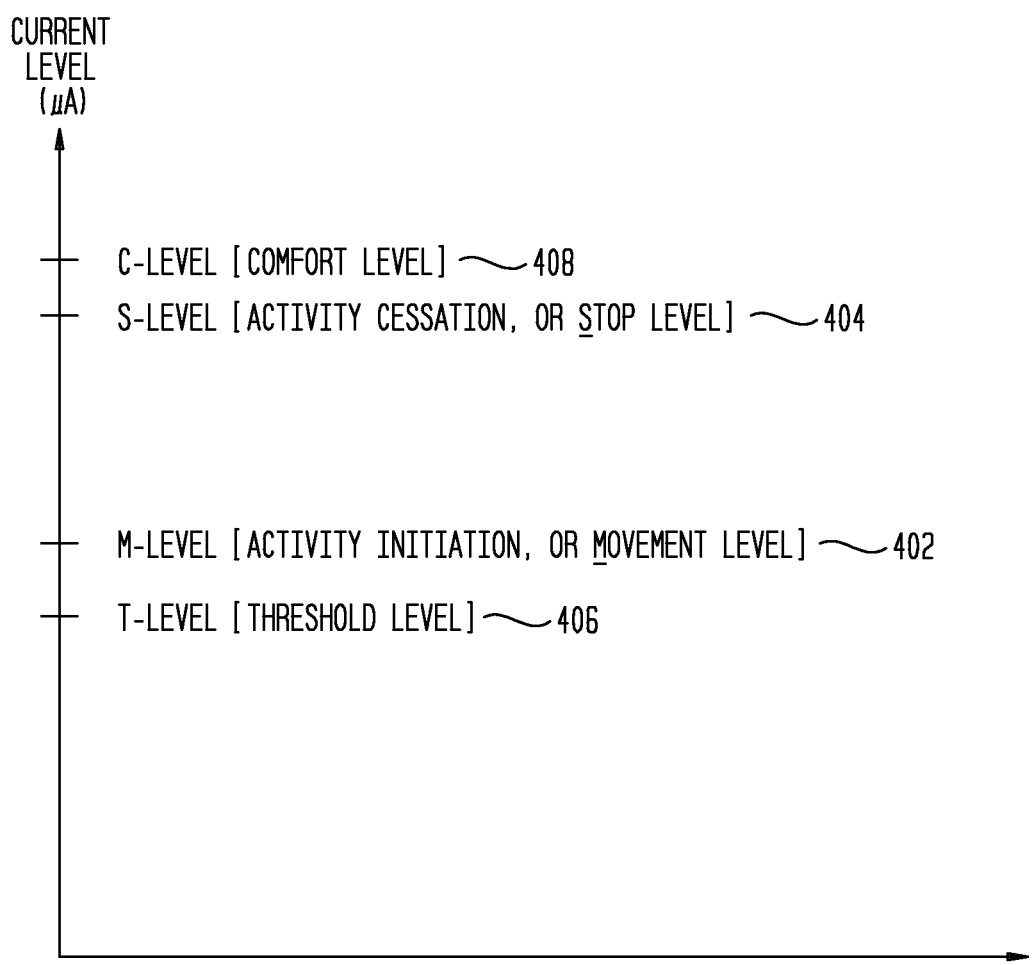
FIG. 4 illustrates the relation between M- and S-levels and T- and C-levels, in accordance with one embodiment of the present invention.

FIG. 4 is graph illustrating the relationship between C-, T-, M- and S-levels. The M-level 402 is most likely below the S-level 404 since it is assumed that the child is more concentrated in a still position, while when moving the child might be concentrating on other things and needs a higher stimulation to get into hearing. It is also assumed that the S- and M-levels will not be the same as the T- and C-levels measured using standard single-electrode psychophysics, but it is expected that both S- and M-levels are different from T- and C-levels, respectively. Most likely, the M-level will be above the T-level, while the S-level may be below or above the C-level, as illustrated in FIG. 4.

M-level 402 and S-level 404 may also be linked to other types of activity of child recipient 162, or to his/her behavior. M-level 402 may be defined, for example, as the stimulation level that causes a change from a low degree of activity to an increased degree of activity. Similarly, S-level 404 may be determined by the stimulation level that causes a change from a relatively high degree of activity to a relatively low degree of activity.

FIG. 5 is a high-level flow chart of the operations performed in accordance with one embodiment of the present invention. The operations identified in FIG. 5 are performed for each selected electrode channel or band of electrodes while the other channels are turned to zero during the process. It should be appreciated that in alternative embodiments of the present invention the M- and S-levels for a number of channels may be determined simultaneously.

At block 502 a plurality of stimulation signals having the same amplitude are applied to the recipient. In this exemplary application, the auditory prosthesis is cochlear implant 100 which applies the electrical stimulation signals to cochlea 132 (FIG. 1) of a child recipient 162 (FIG. 1B) via electrodes 134 (FIG. 1A).

At block 504, inertia data 206 indicating changes in the recipient's physical activity is monitored. As one of ordinary skill in the art would appreciated, IMU 202 typically generates inertia data 206 continuously, in which case at block 504 the inertia data generated concurrently and subsequently to each of the above applications of the stimulation signals is monitored at block 504.

At block 506 a determination is made as to whether the child recipient experienced a change in hearing perception in response to said stimulation signal amplitude based on said inertia data.

At block 508 an operational parameter such as the T- and C-level of the auditory prosthesis is set to the stimulation signal amplitude when changes in recipient activity are determined to have caused a change in hearing perception in the recipient. From the perspective of the present invention, this comprises providing the M-level and/or S-level to fitting system 144 as at least one of either a T-level or C-level of the auditory prosthesis.

FIG. 6 is a flow chart of the operations performed at block 506 above. At block 602, a confidence value is assigned to the amplitude of the applied stimulation signals based on the recipient activity changes indicated in by inertia data 206. Such a confidence value is assigned for each such application.

At block 604, the summation of the assigned confidence values is compared with a predetermined confidence threshold representative of a change in hearing perception.

At block 606 at least one of an M-level and an S-level are set equal to the stimulation signal amplitude when the confidence value of the stimulation signal amplitude indicates that the changes in recipient activity reflect a change in hearing perception due to the applied stimulation signals.

Figure 7B:
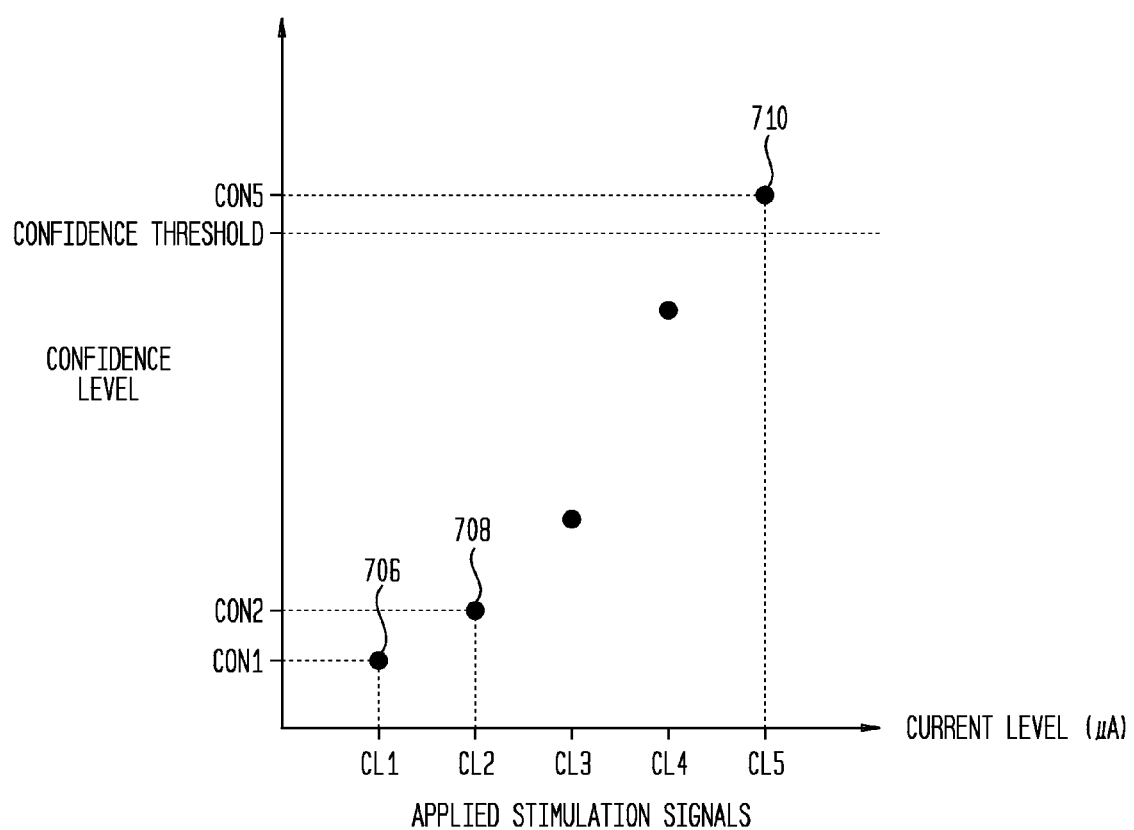
FIG. 7B is the calculated confidence level for each such applies stimulation signal based on the recipient response to that stimulation signal, as illustrated in FIG. 5A.

In one embodiment, the assigned confidence value is incremented or decremented with each successive application of the stimulation signal depending on whether IMU 202 detected a sufficient change in the activity of recipient 162. This is illustrated by an exemplary series of tests conducted to determine the noted M-level in child recipient 162. In FIGS. 7A and 7B. FIG. 7A is a graph illustrating the results of testing five stimulation signals, each applied to the recipient in ten successive tests. FIG. 7B is a graph illustrating the confidence value assigned to the current level of each of the five stimulation signals based on the test results illustrated in FIG. 7A.

The procedure starts with an initial value for the stimulation signal amplitude set to CL1 and the associated confidence value set to some predetermined value such as zero. Referring to FIG. 7A, the stimulation signal having an amplitude represented by current level 1 (CL1) is applied in ten tests. While applying a stimulation signal having an amplitude of CL1, the degree of activity of the child is sensed by IMU 202 and monitored.

When motion is initiated, or when an increase in the degree of activity or behavior is detected by IMU 200, the confidence value for this amplitude is incremented. If, upon stimulation IMU 202 does not detect a significant change in the child's activity, the confidence value may optionally be decreased. For example, in test 1, the change in recipient activity, if any, detected by IMU 202 is determined to be insufficient to be representative of a change in hearing perception. Hence, data point 702 is an open circle. As a result of test 1, the confidence value assigned to the stimulation signal amplitude CL1 is decremented by some predetermined value or, in an alterative embodiment, left unchanged. Conversely, in test 2, the change in recipient activity is determined to be sufficient to be representative of a change in hearing perception. Hence, data point 704 is a filled circle. As a result of test 2, the confidence value assigned to the stimulation signal amplitude CL1 is incremented by some predetermined value. This is continue for the ten tests, and the resulting confidence value CON1 assigned to amplitude CL1 due to the recipient changing activity in two of the ten tests is shown by data point 706 in FIG. 7B.

When the confidence value reaches a predetermined level 700, the current level is retained as the M-level for the channel under consideration. Since CON1 is below predetermined confidence threshold 700, current level CL1 is determined to not be the M-level, and the amplitude of the stimulation signal is increased to CL2, and the tests are repeated. Due to greater quantity of detected changes in recipient activity in response to stimulation signals having a current level of CL2, the assigned confidence value CON2 is greater than CON1. This process is repeated until application of a stimulation signal having an amplitude of CL5 results in a sufficient quantity of recipient responses that the assigned confidence value CON5 is greater than confidence threshold 700, as shown by data point 708 in FIG. 7B. The M-level is then set at current level CL5.

In the above example when the confidence value of the stimulation signal fails to reach a predetermined confidence threshold within a predetermined quantity of iterations (ten), a stimulation signal having a greater amplitude is chosen and the procedure is repeated. In alternative embodiments, such a determination to increase the amplitude of the stimulation signal is made when the predetermined confidence threshold is not attained within a given amount of time, or when the associated confidence level falls below a lower bound.

It should be appreciated that the series of ten tests conduced for each stimulation signal are separated in time to avoid adaptation. Additionally, or alternatively, the amplitude of the applied stimulation signal is held constant while the periodicity or some other characteristic of the stimulation signal is varied to avoid adaptation. Further, when a stimulation signal having another amplitude is tested, there is a delay between the prior series of tests and the latter series of tests to insure accurate recipient responses are detected. It should also be appreciated that the quantity of tests illustrated in FIG. 7A are exemplary only and that any quantity of tests may be implemented which provide sufficient data to assign a confidence value.

Preferably, if the initial current level is above the amplitude which causes a change in recipient activity, then the stimulation signal current level is either decreased to a value that is below the current level that will result in a change in the child's activity. Alternatively, the increase in activity which is monitored is limited to changes in the degree of activity.

Figure 8:
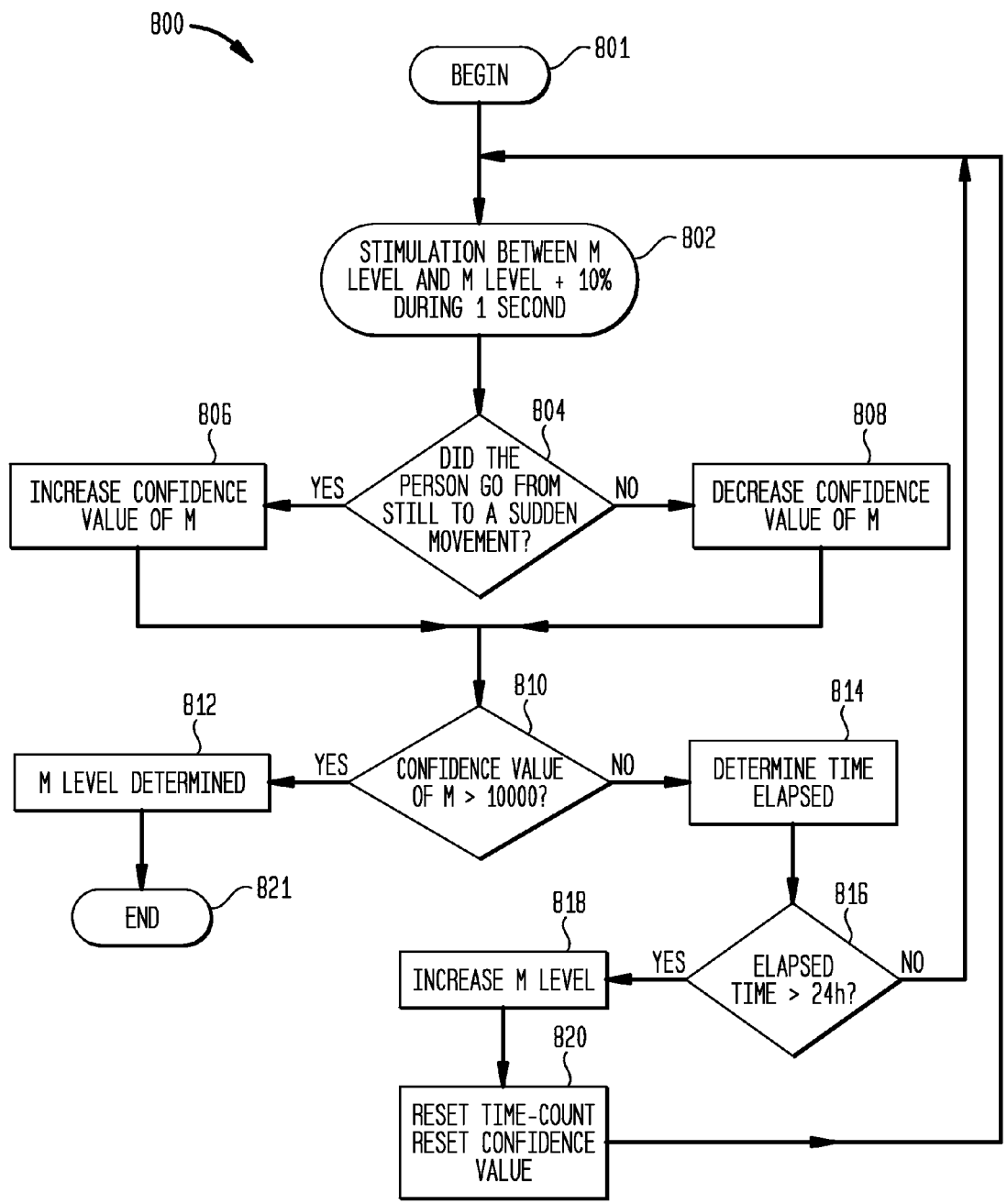
FIG. 8 is a flow chart of the method of automated fitting a stimulation current level, in accordance with one embodiment of the present invention.

FIG. 8 is a detailed flow chart of the operations performed in one embodiment of the present invention. In this example, depending on whether or not an activity change is sensed (block 804) during or after application of an M-level stimulation signal (block 802), the procedure may increase (block 806) or decrease (block 808) the confidence value of the M- or S-level, as shown in FIG. 8. When the confidence value has reached the level of, for example, 10000 (block 810), the M-level is assumed to have been determined (block 812) and is stored in a memory, or provided to a fitting system. On the other hand, if within a given time frame (blocks 814, 816) the confidence value failed to reach the 10000 level, the M level is increased (block 818), the time counter and confidence value are reset (block 820) and procedure 800 is repeated.

Figure 9B:
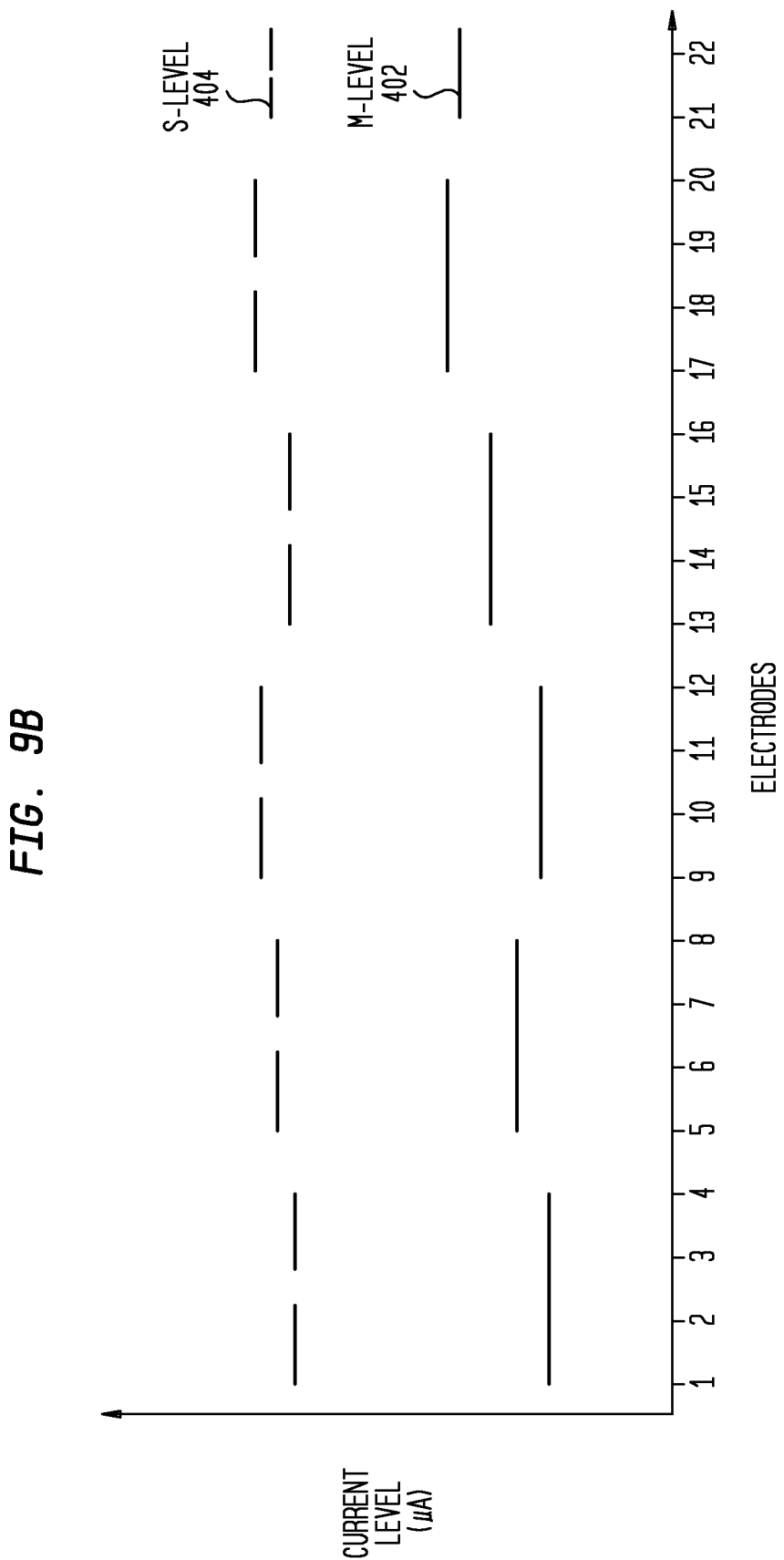
FIG. 9B illustrates the determination of M- and S-levels for bands of electrodes.

The above procedure may be carried out for all channels one-by-one or in a parallel process, where the levels of all channels are turned up together, e.g. in a random or interleaved way. FIG. 9A illustrates the determination of the M- and S-level for individual electrode channels. Alternatively, in order to increase the speed of the process, channels may be combined into bands. For example, in FIG. 9B the 22 electrode channels are divided into 6 bands that are turned on each at a time). The M- and S-level are determined per band, reducing the complexity to 12 measurements (6 bands for each of M- and S-level) instead of 44 (22 bands for each of M- and S-level). The use of bands may enable a faster convergence of the determination of M- and S-levels compared to the one-channel approach of FIG. 9A.

It should be appreciated that in the above exemplary application, the present invention has been implemented to supplement the traditional clinical fitting process. However, the present invention may be implemented outside of the conventional fitting process and without the presence of audiologist/clinician 164. For example, through a user interface to sound processor 316B, a microcontroller in sound processing unit 316B is programmed to run an embodiment of the automated fitting procedure according to the present invention. First, the microcontroller sets stimulation parameters (T- and C-levels) according to default M- and S-levels in the DSP (not shown). Next, a chosen sound implementing the M- or S-level is provided to the DSP, which runs a sound coding strategy and transmits the result via RF link to stimulator unit 126. The sound may consist of only one tone, or a narrow tone band with a given duration (e.g., 1 second). Alternatively, the DSP may be ordered by the microcontroller to transmit directly to stimulator unit 126 a current level stimulation.

Meanwhile, determinator 204 executing in the microcontroller monitors inertia data 206 received from IMU 202. The determinator 204 interprets inertia data 206 measured by IMU 202, and changes the M- or S-level and/or associated confidence value accordingly. The activity detection may be arranged by monitoring on an axis-by-axis basis sections of high energy content. Sections in which the energy is higher than a pre-set threshold are marked as 'active'. If the same section is marked for different axes, this may be a clear indication of a child's activity. An activity change is sensed when on one or more axes a significant change in energy content is measured.

Further features of the present invention are described in U.S. Provisional Patent Application 60/798,312, entitled "Method and Device For Automated Observational Fitting" filed on May 8, 2006, which is hereby incorporated by reference herein.

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A method for fitting an auditory prosthesis to a recipient, comprising:
    applying, via the auditory prosthesis, at least one stimulation signal having one or more characteristics to the recipient;
    generating, via an inertial measurement unit, inertia data indicating changes in the recipient's physical activity;
    assigning, with a determinator, a confidence value to said one or more characteristics of said at least one stimulation signal based on said inertia data, wherein said confidence value is representative of a likelihood a recipient has experienced a change in hearing perception;
    comparing, with the determinator, said confidence value with a predetermined confidence threshold;
    determining, via the determinator, whether said recipient experienced a change in hearing perception in response to the applied at least one stimulation signal based on comparing said confidence value with said predetermined confidence threshold; and
    setting, in the auditory prosthesis, at least one operational parameter of the auditory prosthesis in accordance with one or more characteristics of the at least one applied stimulation signal corresponding to a determined change in hearing perception.

2. The method of claim 1, wherein said auditory prosthesis is a cochlear implant.

3. The method of claim 1, wherein said at least one operational parameter comprises:
    threshold level (T-level); and
    comfort level (C-level).

4. The method of claim 1, wherein said one or more characteristics comprises an amplitude of said applied at least one stimulation signal corresponding to a change in hearing perception.

5. The method of claim 4, wherein said determining comprises:
    assigning a confidence value to said amplitude of said at least one stimulation signal based on said inertia data; and
    comparing said assigned confidence value with a predetermined confidence threshold.

6. The method of claim 1, wherein said generating comprises generating inertia data by one or more of either a gyroscope and accelerometer.

7. The method of claim 1, wherein said at least one stimulation signal comprises one or more of either an electrical stimulation signal, acoustic stimulation signal, and mechanical stimulation signal.

8. The method of claim 1, wherein the setting comprises:
    setting at least one of an movement level (M-level) and an stop level (S-level) in accordance with an amplitude of said applied at least one stimulation signal when said changes in said recipient's activity comprises an increase or decrease in recipient's activity, respectively, representative of a hearing perception experienced determined to be in response to said applied at least one stimulation signal.

9. The method of claim 8, wherein setting an operational parameter of the auditory prosthesis comprises:
    providing at least one of said M-level and said S-level to a fitting system as at least one of either a threshold level (T-level) or comfort level (C-level) of the auditory prosthesis based on a manner in which said at least one of said M-level and said S-level are determined.

10. The method of claim 1,
wherein said one or more characteristics comprises an amplitude of said applied at least one stimulation signal corresponding to a determined change in hearing perception each having substantially the same amplitude,
wherein said applying, generating and determining are performed iteratively with each of said at least one stimulation signals until a predetermined confidence value is obtained.

11. The method of claim 1, wherein said change in recipient's activity comprises one or more of the group consisting of:
an increase in recipient's activity; and
a decrease in recipient's activity.

12. The method of claim 11, wherein said increase in recipient's comprises at least one of the group consisting of:
an initiation of recipient activity; and
an increase from a relatively lower degree of activity to a relatively greater degree of activity.

13. The method of claim 11, wherein said decrease in recipient's activity comprises at least one of the group consisting of:
a cessation of recipient activity;
an decrease from a relatively higher degree of activity to a relatively lower degree of activity.

14. A system for providing at least one operational parameter to a fitting system of an auditory prosthesis of a recipient, comprising:
an inertial measurement unit constructed and arranged to generate inertia data indicating changes in the recipient's physical activity; and
a determinator configured to determine whether said recipient experienced a change in hearing perception in response to applied stimulation signals based on said inertia data, and configured to assign a confidence value to said amplitude of said plurality of said stimulation signals based on said recipient activity changes; and compare said assigned confidence value with a predetermined confidence threshold representative of a change in hearing perception.

15. The system of claim 14, wherein said auditory prosthesis is a cochlear implant.

16. The system of claim 14, wherein said at least one operational parameter comprises:
threshold level (T-level); and
comfort level (C-level).

17. The method of claim 14, wherein said inertial measurement unit comprises one or more sensors of the group consisting of gyroscopes and accelerometers.

18. The system of claim 14, wherein the fitting system is configured to set an operational parameter of the auditory prosthesis in accordance with one or more characteristics of said applied stimulation signals, and said one or more characteristics of said applied stimulation signals comprises an amplitude of said stimulation signals.

19. The system of claim 14, wherein said plurality of stimulation signals comprises one or more of either electrical stimulation signals, acoustic stimulation signals, and mechanical stimulation signals.

20. The system of claim 14, wherein to determine whether said recipient experienced a change in hearing perception in response to said stimulation signal based on said inertia data, said determinator is configured to set at least one of an movement level (M-level) and an stop level (S-level) in accordance with an amplitude of said stimulation signals when said changes in said recipient activity comprises an increase or decrease in recipient activity, respectively, representative of a hearing perception experienced in response to said stimulation signals.

21. The system of claim 20, wherein said determinator is further configure to provide at least one of said M-level and said S-level to a fitting system as at least one of either a threshold level (T-level) or comfort level (C-level) of the auditory prosthesis based on a manner in which said at least one of said M-level and said S-level are determined.

22. The system of claim 14, wherein said change in recipient activity comprises one or more of the group consisting of:
an increase in recipient activity; and
a decrease in recipient activity.

23. The system of claim 22, wherein said increase in recipient activity comprises at least one of the group consisting of:
a initiation of recipient activity;
an increase from a relatively lower degree of activity to a relatively greater degree of activity.

24. The system of claim 22, wherein said increase in recipient activity comprises at least one of the group consisting of:
a cessation of recipient activity;
an decrease from a relatively higher degree of activity to a relatively lower degree of activity.

25. A system for automatically determining operational parameters of an auditory prosthesis for a recipient, comprising:
an apparatus configured to cause the auditory prosthesis to apply at least one stimulation signal having one or more characteristics to the recipient;
an inertial measurement unit configured to generate inertia data indicating changes in the recipient's physical activity; and
a determinator configured to assign a confidence value to said one or more characteristics of said at least one stimulation signal based on said inertia data, wherein said confidence value is representative of a likelihood a recipient has experienced a change in hearing perception, and configured to determine whether said recipient experienced a change in hearing perception in response to said stimulation signals based on comparing the determined confidence value with a predetermined confidence threshold.

26. The system of claim 25, further comprising:
an apparatus configured to set an operational parameter of the auditory prosthesis in accordance with one or more characteristics of said stimulation signals when said determinator determines that changes in said recipient activity reflect a change in hearing perception in the recipient in response to said stimulation signals.

27. The system of claim 26, wherein said one or more characteristics of said stimulation signals comprises an amplitude of said stimulation signals.

28. The system of claim 25, wherein the auditory prosthesis is a cochlear implant.

29. The system of claim 25, wherein said operational parameters comprise one or more of either a threshold level (T-level) and a comfort level (C-level).

30. The system of claim 25, wherein said inertial measurement unit comprises one or more sensors of the group consisting of gyroscopes and accelerometers.

31. The system of claim 25, wherein said plurality of stimulation signals comprises one or more of either electrical stimulation signals, acoustic stimulation signals, and mechanical stimulation signals.

32. The system of claim 25, wherein to determine whether said recipient experienced a change in hearing perception in response to said stimulation signal based on said inertia data, said determinator is configured to set at least one of an movement level (M-level) and an stop level (S-level) in accordance with an amplitude of said stimulation signals when said changes in said recipient activity comprises an increase or decrease in recipient activity, respectively, representative of a hearing perception experienced in response to said stimulation signals.

33. The system of claim 32, wherein said determinator is further configure to provide at least one of said M-level and said S-level to a fitting system as at least one of either a threshold level (T-level) or comfort level (C-level) of the auditory prosthesis based on a manner in which said at least one of said M-level and said S-level are determined.

34. The system of claim 25, wherein said change in recipient activity comprises one or more of the group consisting of:
  an increase in recipient activity; and
  a decrease in recipient activity.

35. The system of claim 34, wherein said increase in recipient activity comprises at least one of the group consisting of:
  an initiation of recipient activity; and
  an increase from a relatively lower degree of activity to a relatively greater degree of activity.

36. The system of claim 34, wherein said decrease in recipient activity comprises at least one of the group consisting of:
  a cessation of recipient activity;
  a decrease from a relatively higher degree of activity to a relatively lower degree of activity.

37. The system of claim 25, wherein one or more characteristics of the amplitude of said applied at least one stimulation signal corresponds to a determined change in hearing perception and wherein said detecting and determining are performed iteratively with each of said at least one stimulation signals until a confidence value is assigned.

38. An apparatus for fitting an auditory prosthesis to a recipient, comprising:
  means for applying at least one stimulation signal having one or more characteristics to the recipient;
  means for generating inertia data indicating changes in the recipient's physical activity;
  means for assigning a confidence value to said one or more characteristics of said at least one stimulation signal based on said inertia data, wherein said confidence value is representative of a likelihood a recipient has experienced a change in hearing perception;
  means for determining whether said recipient experienced a change in hearing perception in response to said stimulation signal based on comparing said confidence value with said predetermined confidence threshold.

39. The apparatus of claim 38, further comprising:
  means for setting an operational parameter of the auditory prosthesis in accordance with one or more characteristics of said at least one stimulation signal when said changes in said recipient activity are determined to have caused a change in hearing perception in the recipient.

40. The apparatus of claim 38, wherein said auditory prosthesis is a cochlear implant.

41. The apparatus of claim 38, wherein said operational parameters comprise threshold level (T-level) or comfort level (C-level).

42. The apparatus of claim 38, wherein said one or more characteristics of said at least one stimulation signal comprises an amplitude of said at least one stimulation signal.

43. The apparatus of claim 38, wherein said at least one stimulation signal comprises one or more of either an electrical stimulation signal, acoustic stimulation signal, and mechanical stimulation signal.

44. The apparatus of claim 38, wherein said means for determining whether said recipient experienced a change in hearing perception in response to said stimulation signal based on said inertia data comprises:
  means for setting at least one of an movement level (M-level) and an stop level (S-level) in accordance with an amplitude of said at least one stimulation signal when said changes in said recipient activity comprises an increase or decrease in recipient activity, respectively, representative of a hearing perception experienced in response to said stimulation signals.

45. The apparatus of claim 44, wherein means for setting an operational parameter of the auditory prosthesis comprises:
  providing at least one of said M-level and said S-level to a fitting system as at least one of either a threshold level (T-level) or comfort level (C-level) of the auditory prosthesis based on a manner in which said at least one of said M-level and said S-level are determined.

* * * * *